US008946618B2

(12) United States Patent
Kalitsis et al.

(10) Patent No.: US 8,946,618 B2
(45) Date of Patent: Feb. 3, 2015

(54) SYSTEM FOR DETECTING ONE OR MORE PREDETERMINED OPTICALLY DERIVABLE CHARACTERISTICS OF A SAMPLE

(75) Inventors: John Kalitsis, North Ryde (AU); Ian John Wesley, North Ryde (AU); William Carpenter, North Ryde (AU)

(73) Assignee: Rosewood Research Pty Ltd, New South Wales (AU)

( * ) Notice: Subject to any disclaimer, the term of this patent is extended or adjusted under 35 U.S.C. 154(b) by 0 days.

(21) Appl. No.: 13/451,127

(22) Filed: Apr. 19, 2012

(65) Prior Publication Data

US 2012/0265729 A1    Oct. 18, 2012

Related U.S. Application Data

(62) Division of application No. 12/280,348, filed as application No. PCT/AU2007/000192 on Feb. 21, 2007, now Pat. No. 8,183,548.

(30) Foreign Application Priority Data

Feb. 21, 2006 (AU) ................................ 2006200712

(51) Int. Cl.
*H01J 3/14* (2006.01)
*G01N 21/359* (2014.01)
(Continued)

(52) U.S. Cl.
CPC .......... *G01N 21/359* (2013.01); *G01N 21/3563* (2013.01); *G01N 33/10* (2013.01); *G01N 2021/8592* (2013.01); *G01N 2201/0221* (2013.01)
USPC ....................................................... 250/216

(58) Field of Classification Search
CPC ........ G02B 6/2931; G01J 3/18; G01J 3/0202; G01J 3/0272
USPC ....................................................... 250/216
See application file for complete search history.

(56) References Cited

U.S. PATENT DOCUMENTS 4,850,706 A    7/1989  Mikes
4,997,280 A    3/1991  Norris
(Continued)

FOREIGN PATENT DOCUMENTS

EP    0240185 A2    10/1987
EP    0596600 A1    5/1994
(Continued)

OTHER PUBLICATIONS

Derwent Abstract Accession No. 89-329678/45, Class V07, JP 1246-511-A (Toshiba KK) Oct. 2, 1989. See entire Abstract.
(Continued)

*Primary Examiner* — Thanh Luu
(74) *Attorney, Agent, or Firm* — Novak Druce Connolly Bove + Quigg LLP

(57) ABSTRACT

A field use optical grain characterizing system (101) includes a generally rectangular prismatic composite body (102) that defines a component cavity (103). A substantially vertical elongate channel (104) extends within cavity (103) for housing a grain sample (not shown). An electromagnetic radiation source, in the form of a 12 Volt halogen lamp (105), is disposed within cavity (103.) for directing NIR light into channel (104). An optical detection system (107) is disposed within cavity (103) for sensing selected light emerging from channel (104) and for providing a sensor signal. A processor, which is included within detection system (107), is also disposed within cavity (103) and is responsive to the sensor signal for providing data indicative of a characteristic parameter of the grain sample. A display device, in the form of a 5.7-inch touch screen LCD display (108), is connected with body (102) for selectively presenting the data.

14 Claims, 21 Drawing Sheets

(51) Int. Cl.
*G01N 21/3563* (2014.01)
*G01N 33/10* (2006.01)
*G01N 21/85* (2006.01)

(56) References Cited

U.S. PATENT DOCUMENTS

| | | | |
|---|---|---|---|
| 5,132,538 A | 7/1992 | Norris | |
| 5,425,118 A | 6/1995 | Sugihara et al. | |
| 5,589,717 A | 12/1996 | Chau | |
| 5,751,421 A | 5/1998 | Wright et al. | |
| 5,818,045 A | 10/1998 | Mark et al. | |
| 5,880,834 A | 3/1999 | Chrisp | |
| 6,031,608 A | 2/2000 | VonBargen et al. | |
| 6,172,822 B1* | 1/2001 | Belliveau et al. | 359/819 |
| 6,322,223 B1 | 11/2001 | Smith et al. | |
| 6,765,948 B2* | 7/2004 | Murry et al. | 372/107 |
| 6,870,616 B2 | 3/2005 | Jung et al. | |
| 7,085,492 B2* | 8/2006 | Ibsen et al. | 398/38 |
| 2002/0181102 A1* | 12/2002 | Leyva et al. | 359/495 |

FOREIGN PATENT DOCUMENTS

| | | |
|---|---|---|
| WO | WO-99/40419 | 8/1999 |
| WO | WO-01/35076 A1 | 5/2001 |
| WO | WO-0240967 A1 | 5/2002 |
| WO | WO-0240968 A1 | 5/2002 |

OTHER PUBLICATIONS

"International Search Report," issued by the International Searching Authority in connection with International Patent Application No. PCT/AU2007/000192, mailed on Jun. 26, 2007 (4 pages).

"Written Opinion," issued by the International Searching Authority in connection with International Patent Application No. PCT/AU2007/000192, mailed on Jun. 26, 2007 (6 pages).

"International Preliminary Report on Patentability," issued by the International Searching Authority in connection with International Patent Application No. PCT/AU2007/000192, mailed on Aug. 26, 2008 (7 pages).

European Office Action dated Feb. 7, 2014.

* cited by examiner

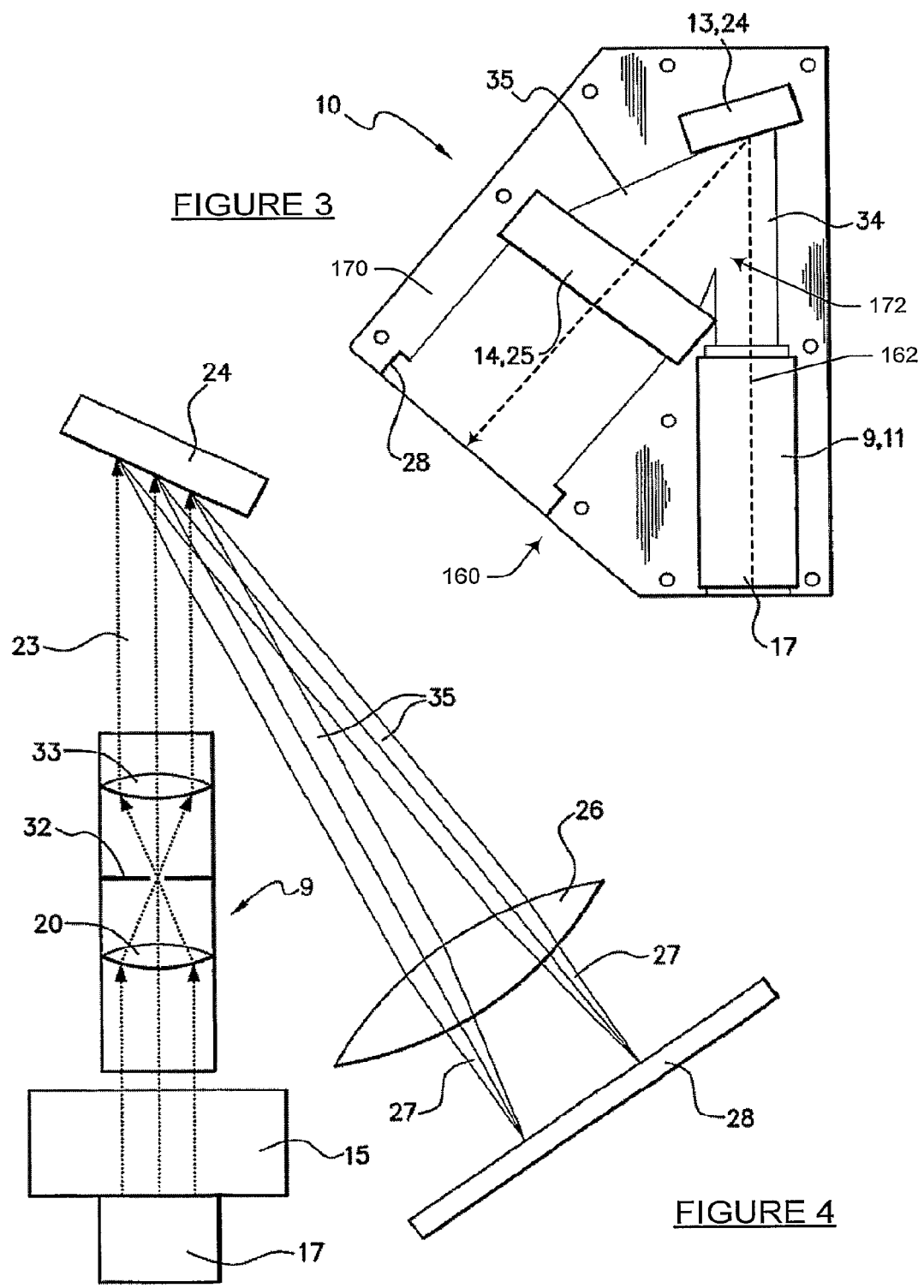

SYSTEM FOR DETECTING ONE OR MORE PREDETERMINED OPTICALLY DERIVABLE CHARACTERISTICS OF A SAMPLE

FIELD OF THE INVENTION

The present invention relates to a system for detecting one or more predetermined optically derivable characteristics of a sample.

The invention has been primarily developed as a portable optical grain characterising system and will be described hereinafter with reference to this application. However, it will be appreciated that the invention is not limited to this particular field of use and, for example, may be used for analysing other products that are responsive to illumination by light for measurably varying a characteristic of the light that allows a parameter to be monitored.

BACKGROUND OF THE INVENTION

Any discussion of the prior art throughout the specification should in no way be considered as an admission that such prior art is widely known or forms part of common general knowledge in the field.

It is known that a product such as grain can be monitored by an optical methodology to determine, for example, the percentage of moisture present in the grain. This is a key economic factor for the purpose of quality assessment and determination of any process steps that might be required such as drying of the grain during initial storage. This field is one to which embodiments of the invention can be applied. Portable moisture meters suitable for in-field use are known but there is considerable difficulty in aligning the output from such moisture meters with laboratory type equipment using sophisticated and expensive near infrared technology which has been developed for use at grain receival points.

Relatively expensive equipment is known for use in laboratory and receival conditions to measure the moisture in grain with sufficient accuracy for trading.

It is known that the amount of electromagnetic radiation, and more usually visible light or near IR radiation, absorbed at a particular typically narrow range of wavelengths is proportional to the concentration of a light absorbing component or species and the path length of the light through the sample. Accordingly, by illuminating a sample with light an analysis of the transmitted light through the sample at appropriate wavelengths can be affected to determine the concentration of the relevant chemical component such as water. Physical calibration with a range of samples with known properties is required. Calibration precisely relates the amount of the light absorbed with the concentration of the absorbing species at the relevant range of wavelengths. The range of wavelengths more commonly used is selected from the near infrared, the mid infra-red or the visible portion of the electromagnetic spectrum.

One example applicable to the task of measuring moisture in grain is described in U.S. Pat. No. 6,031,608 (Van Bargen and Norris) which describes an instrument operating at near infrared frequencies ("NIR") which are about 780 nm to about 2,500 nm. The instrument uses a spherical diffraction grating from which light is reflected over a spread of frequencies. The diffraction grating causes the incident light to be reflected at different angles depending on the wavelength of the incident light. By positioning an optical detector at the appropriate position, the intensity of light at a specific wavelength can be measured. The measurements can then be used to develop the relationship between concentration of absorbing species such as moisture and light absorbance.

In U.S. Pat. No. 6,031,608 the grating is moved in an oscillatory manner so that a selected very narrow bandwidth of light is incident on a sample from which there is reflection to a detector. At any instant the amplitude of light on the detector is measured with respect to the incident frequency. This gives a measure of the degree of absorption of the illuminated sample and thus determines a characteristic of the sample. For example, the sample may be a specimen of grain in which the moisture content is to be determined. It is well known that an absorption peak in the spectrum of grain related to water is spread around about 965 nm. However frequencies either side of this centre frequency must also be examined in order to determine, in this case, the moisture content. This apparatus is complex with its moving parts and most significantly is a laboratory type instrument requiring meticulous calibration so that the raw data for a signal (the strength recorded at different frequencies) can be processed in accordance with a relationship governed by the particular piece of equipment to determine moisture content. U.S. Pat. No. 6,031,608 deals with a particular development to offset the axis of oscillation from a tangent to the spherical diffraction grating and thus is aimed at solving a problem particular to complex machines in which oscillation occurs to scan through the frequency spectrum.

Other examples in the field are:

| U.S. Pat. No. | Inventor |
| --- | --- |
| 5,589,717 | Chiu Chau |
| 5,880,834 | Michael P Chrisp |
| 4,850,706 | Thomas Mikes |
| 4,997,280 | Karl Norris |
| 5,132,538 | Karl Norris |

In addition, PCT applications WO 02/40968 and WO 02/40967 have disclosures relating to grain monitoring by use of light.

The abovementioned patent specifications can be located by appropriate searching but recognition of these documents is not to be taken as admission that the content is actually known generally or forms part of the general knowledge to persons ordinarily skilled in the field.

Particularly for applications in the food and beverage area spectrographic monitoring techniques are widely known. A leading text is "Practical NIR Spectroscopy" (Osborne et al) published by Longman Scientific and Technical. Page 29 of the 2nd Edition demonstrates that various components have observed characterising absorption bands at NIR frequencies. By using the reciprocal of reflectance or transmittance in presentations and especially graphic presentations, then the absorption is characterised by a "peak" centred on a main frequency.

The present invention is directed to new and alternative approaches to spectroscopy especially applicable to the agricultural, and beverage industries but not necessarily confined thereto. One important application of some of the preferred embodiments of the invention that will be described in detail is the monitoring of moisture in grain. However, the equipment and principles described herein are equally applicable to monitoring other characteristics, such as protein in grain, particularly in the NIR portion of the spectrum.

A critical limitation pointed out by the present inventors is that equipment available on the market is essentially laboratory scale equipment which is capable of highly accurate performance but is essentially not suitable for field use. Furthermore, and most importantly, it is relatively expensive equipment particularly because of the expensive and careful alignment steps needed for each and every instrument so that the output data from all the instruments is consistent. That is, considerable effort and expense is expended in ensuring that all the instruments will provide consistent results for a given sample.

The inventors have observed an important un-met need for equipment which can be robust, relatively inexpensive, easily manufactured and suitable for field use, for example, by farmers who need to quickly and with reasonable accuracy determine characteristics such as protein and moisture content in grain prior to harvesting and shipment to a receiving station. If the grain has excessive moisture, it may be rejected at great economic loss to the farmer or if the moisture is somewhat high then the price will be downgraded.

SUMMARY OF THE INVENTION

It is an object of the present invention to overcome or ameliorate at least one of the disadvantages of the prior art, or to provide a useful alternative.

According to a first aspect of the present invention there is provided a system for detecting one or more predetermined characteristics of a grain sample, the system including:
(a) a detection zone for containing the sample;
(b) a radiation source for directing light into the zone;
(c) a plurality of detectors each for providing a sensor signal in response to selected light emerging from the zone;
(d) a controller that is responsive to the sensor signals for: selectively adjusting the detectors to provide respective adjusted sensor signals; and generating an adjustment signal; and
(e) a processor that is responsive to the adjusted sensor signals and the adjustment signal for providing data indicative of the one or more predetermined characteristic of the sample.

According to a second aspect of the invention there is provided a rigid base plate including a sequence of formations $F_1, F_2, \ldots, F_n$ for receiving respective optical components $C_1, C_2, \ldots, C_n$ to define an optical path, wherein $n \geq 2$ and at least the first formation $F_1$ sealingly receives its respective component $C_1$.

In an embodiment the last formation, $F_n$, sealingly receives component $C_n$. Preferably, the base plate includes a mounting plate for at least partially defining the formations and a top plate for sealingly engaging with the mounting plate, wherein the mounting plate and the base plate collectively define a cavity for containing components $C_1, C_2, \ldots, C_n$. More preferably, the top plate and mounting plate each at least partially define the formations. Even more preferably, the mounting plate and the top plate substantially mirror each other. In an embodiment the mounting plate and the top plate include respective sealing faces that, in use, are abutted to effect the sealing engagement.

In an embodiment the mounting plate and the top plate collectively define along the path an entry window and an exit window. Preferably, $F_1$ and $F_n$ are adjacent to the entry window and the exit window respectively.

In an embodiment the top plate and the bottom plate are formed of a plastics material. Preferably, the plastics material is acetal. However, in other embodiments alternative materials are used.

In an embodiment one or both of the top plate and the bottom plate are moulded. Preferably, one or both of the top plate and the bottom plate are injection moulded.

In an embodiment the base plate includes a sealant for extending between component $C_1$ and formation $F_1$. Preferably, component $C_1$ includes a periphery and the sealant is a bead for extending around the periphery.

In an embodiment the base plate is IP65-proof sealed.

In an embodiment the base plate is formed from a material having a low coefficient of thermal expansion.

According to a third aspect of the invention there is provided a field-use optical grain characterising system including:
(a) a body for defining a cavity;
(b) a channel in the body for housing a grain sample;
(c) a radiation source disposed within the cavity for directing light into the channel;
(d) an optical detection system disposed within the cavity for sensing selected light emerging from the channel and for providing a sensor signal;
(e) a processor disposed within the cavity and being responsive to the sensor signal for providing data indicative of a characteristic parameter of the grain sample; and
(f) a display device connected with the body for selectively presenting the data.

In an embodiment the display device includes a control interface. Preferably, the control interface is a touch-screen. More preferably, the display device includes fixed indicia adjacent to the touch-screen. Even more preferably, the touch-screen, in use, is inclined relative to the horizontal.

In an embodiment the touch-screen is inclined relative to the horizontal by between about 25° to 30°. Preferably, the touch-screen includes an exposed display protection surface. More preferably, the protection surface is formed of a robust material that is substantially transparent to visible light.

In an embodiment the screen is a colour screen.

In an embodiment the body includes a sample drawer for receiving the sample from the channel. Preferably, the drawer is selectively received by the body in one of two orientations, wherein in a first of the orientations the sample is received and captively retained within the drawer, and in the other of the orientations the sample is received directed away from the drawer. More preferably, the volume of the drawer is approximately 400 ml.

In an embodiment the system includes a power source. Preferably, the power source includes a battery pack. More preferably, the battery pack includes a 12 Volt lithium ion battery. Even more preferably, the battery is rechargeable.

According to a fourth aspect of the invention there is provided a field-use optical characterising system including:
(a) a body defining a cavity;
(b) a channel for housing a sample;
(c) a radiation source disposed within the cavity for directing light into the channel;
(d) an optical detection system disposed within the cavity for sensing selected light emerging from the channel and for providing a sensor signal;
(e) a processor disposed within the cavity that is responsive to the sensor signal for providing data indicative of a characteristic parameter of the grain sample; and
(f) a display device connected with the body for selectively presenting the data.

According to a fifth aspect of the invention there is provided a system for detecting one or more predetermined optically derivable characteristics of a sample, the system including:
(a) a detection zone for containing the sample;
(b) a radiation source for directing light into the zone;
(c) a plurality of detectors each for providing a sensor signal in response to selected light emerging from the zone;

(d) a controller that is responsive to the sensor signals for: selectively adjusting the detectors to provide respective adjusted sensor signals; and generating an adjustment signal; and (e) a processor that is responsive to the adjusted sensor signals and the adjustment signal for providing data indicative of the one or more predetermined characteristic of the sample.

According to a sixth aspect of the invention there is provide an optical characterising system including:
(a) a body for defining a cavity;
(b) a channel in the body for housing a sample;
(c) a radiation source disposed within the cavity for directing light into the channel;
(d) an optical detection system disposed within the cavity for sensing selected light emerging from the channel and for providing a sensor signal;
(e) a processor disposed within the cavity that is responsive to the sensor signal for providing data indicative of a characteristic parameter of the grain sample; and
(f) a display device connected with the body for selectively presenting the data.

According to a seventh aspect of the invention there is provided a portable optical characterising system including:
(a) a body for defining a cavity;
(b) a channel in the body for housing a sample;
(c) a radiation source disposed within the cavity for directing light into the channel;
(d) an optical detection system disposed within the cavity for sensing selected light emerging from the channel and for providing a sensor signal;
(e) a processor disposed within the cavity that is responsive to the sensor signal for providing data indicative of a characteristic parameter of the grain sample; and
(f) a display device connected with the body for selectively presenting the data.

According to an eighth aspect of the invention there is provided an optical characterising system including:
(a) a body for defining a cavity;
(b) a channel in the body for housing a sample;
(c) a radiation source disposed within the cavity for directing light into the channel;
(d) an optical detection system disposed within the cavity for sensing selected light emerging from the channel and for providing a sensor signal;
(e) a processor disposed within the cavity that is responsive to the sensor signal for providing data indicative of a characteristic parameter of the sample; and
(f) a communications interface within the cavity for allowing communication with at least one remote device.

In an embodiment the processor is responsive to operating software and the communication with the remote device allows updating of the software. Preferably, the communication includes providing the remote device with the data.

According to a ninth aspect of the invention there is provided a system for operating a set of optical characterisation instruments that each include operating software and which each provide operating data, the system including:
(a) a database for maintaining data records indicative of the instruments; and
(b) a processor that is responsive to the data records for communicating with the instruments to access and/or modify one or both of the operating data and the operating software.

According to a tenth aspect of the invention there is provided an optical system for analysing an output spectrum in the NIR from a sample exposed to light and wherein the output spectrum correlates with a selected parameter for the sample, the system comprising:
(a) a light source;
(b) a sample holder;
(c) a detector having an array of elements, each element being adapted to provide an output signal to a signal processor and representative of the amplitude of the received light incident on the element from a portion of the NIR spectrum at and around an absorption peak: characterizing the selected parameter of the sample;
(d) a signal processor for processing signals from the array of elements and using calibration algorithm for such systems to compute an output signal representative of the selected parameter of the sample; and
(e) a spectrographic system including optical components for processing light from the sample to the detector, the spectrographic system having:
  i. a diffraction grating;
  ii. optical means for applying light from the sample onto the diffraction grating such that the portion of the NIR spectrum processed by the diffraction grating includes at least a peak of the portion of the spectrum of interest and correlating with the selected parameter;
  iii. an optical path for applying the output from the diffraction grating to be spread onto and received by respective elements of the detector such that the output from each detector is arranged to provide an output signal correlating with a segment of an absorption peak of interest;
  iv. means for applying a centre segment of the absorption peak in the spectrum portion of interest to a selected element of the detector;
  v. means for applying selected narrow band segments of the spectrum adjacent to the centre of the peak to respective adjacent elements of the detector, whereby numerical values of samples of the peak profile are obtained and can be integrated by the signal processor in accordance with a calibration algorithm to provide the desired output; and
  vi. a rigid plate-like body with apertures in to which the optical components are fitted to be accurately positioned and held, wherein: the body is of a material having stability and a low coefficient of thermal expansion over 0° C. to 50° C. and has a thickness of around 12 mm; and that arrangements for mounting the optical components have tolerances which are not precision tolerances.

BRIEF DESCRIPTION OF THE DRAWINGS

Preferred embodiments of the invention will now be described, by way of example only, with reference to the accompanying drawings in which:

FIG. 3 is a plan view showing a second embodiment of a rigid mounting plate for mounting critical components;

FIG. 4 is a plan diagram sectioned through the central plane of the optical paths illustrating operation of the device having components mounted in a base plate of FIG. 3;

PREFERRED EMBODIMENTS OF THE INVENTION

Figure 1:
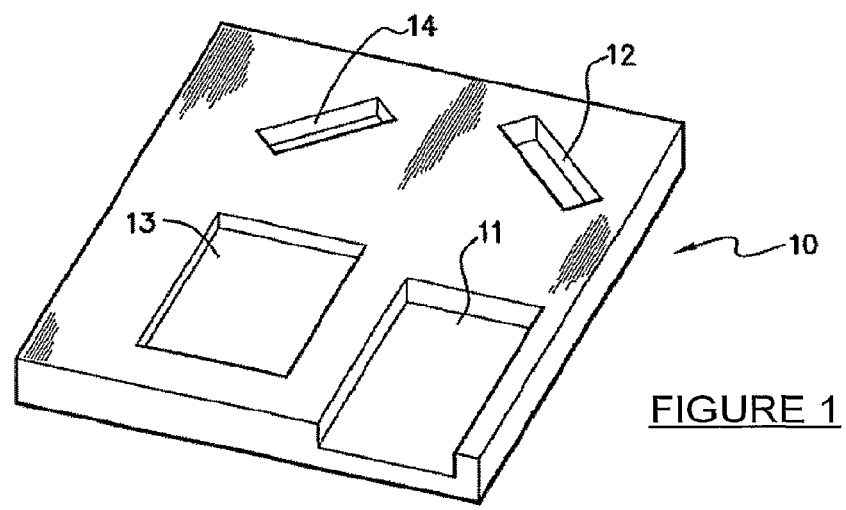
FIG. 1 is an oblique view of a rigid mounting plate for mounting critical components of a first embodiment.

FIG. 1 shows a thick base plate 10 of a stable plastic material such as PVC which is typically 12 mm thick. It has deep mounting recesses 11 to 14 respectively for an optical barrel, a concave mirror, a reflection diffraction grating, and a focusing lens. The base plate 10 encapsulates these components by placement of a top plate 10, which is substantially a mirror image of the base plate, on top of the base plate.

Figure 2:
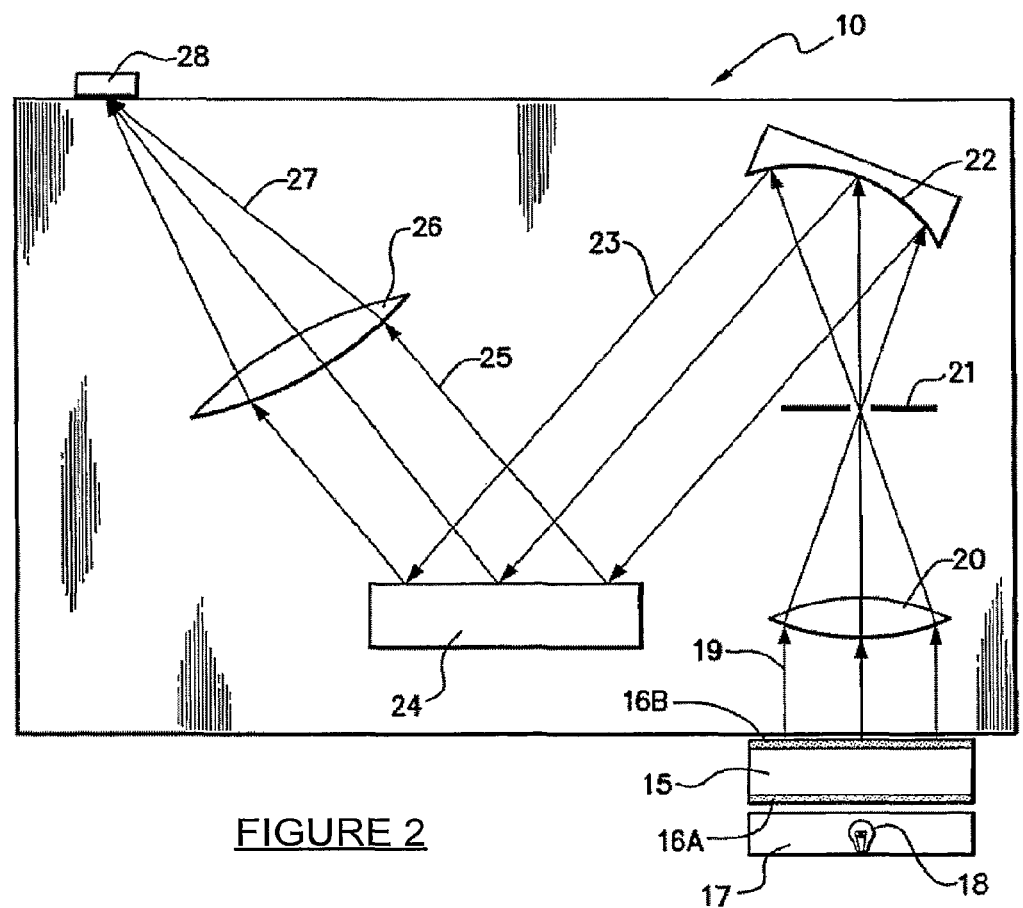
FIG. 2 is a plan diagram sectioned through the central plane of the optical paths illustrating operation of the device having components mounted in a base plate of FIG. 1.

Referring now to FIG. 2, more detail is shown schematically of the components in the optical system. The apparatus has a sample container 15 mounted adjacent to the base plate 8 and adapted to contain a sample such as grain. A light source 17 having a halogen bulb 18 is mounted adjacent to the sample container 15 so that light from the bulb 18 passes through an inlet window 16A, is transmitted through the sample, and out through an outlet window 16B to form a beam 19 affected by the sample. This beam is incident on the optical barrel which comprises a lens 20 and a slit 21. The barrel is mounted in recess 11 shown in FIG. 1. The beam then is incident on a concave mirror 22 mounted in slot 21, which converts the incident diverging beam into a reflected parallel beam 23. The parallel beam extends parallel to the base plate 10 to be incident at an angle of 36.4 degrees from the general central plane of the beam on a reflection diffraction grating 24 mounted in recess 13 shown in FIG. 1. The grating in a desirable embodiment has 1200 lines per mm, the lines being horizontally extending whereby the reflected beam 25 is also parallel to the base plate 8 for the peak frequency of interest. The beam 25 passes through a focusing lens 26 which is mounted in recess 14 and produces a focused beam 27 in the NIR onto a detector 28 having a vertical array of adjacent detector elements or pixels which, in a useful embodiment, are relatively large and dimensioned approximately 5 mm by 1 mm.

In a most useful embodiment, simple vertical adjustment of the detector array permits the centre pixel to be centred on the peak of the absorption curve of interest. Typically each pixel will detect a narrow band of about 13 nm and provide an output signal of amplitude proportional to the detected light in the frequency band.

An electronic control system is provided with signal processing from the pixels to offer values which can be measured and compared with standard stored data. This provides an output which is indicative of the parameter being investigated, for example, moisture in grain.

The illustrated embodiment is best implemented with the diffracted light and the incident light both in a plane parallel to the mounting plate. The wavelength for moisture is 965 nm. Utilising the equation below, it is calculated that to achieve a diffraction angle parallel to the incident light angle the grating WIII need to be mounted at 35.4° for moisture detection. At this angle, light of a wavelength of 485 nm will have a second order diffraction angle equal to 35.4°. For this reason a cut-off filter removing this wavelength is required and should be included in the system, although omitted from the drawings for clarity.

The equation defining grating performance is:

$$m\lambda = d(\sin \alpha + \sin \beta)$$

where:
m=diffraction order;
$\lambda$=wavelength;
d=groove spacing on diffraction grating;
$\alpha$=incident wave angle; and
$\beta$=diffraction wave angle.

The inventors have analysed tolerances for mounting the grating and found that a 1° variation in the angle of mounting results in an adjustment requirement of 0.87 mm at the detector. Thus high precision engineering is not required and simple linear adjustment of the detector is all that is necessary.

In the illustrated embodiment, a focal length of 100 mm was chosen. It was found that the distance from the focusing lens 26 to the detector could be 100 mm (±5 mm) without significant degradation of performance arising. For example, for a 10.4% moisture sample, accurate determination occurred with a distance of 100 mm, a 0.2% error at 1 mm variation and 1.9% error at 5 mm variation. With a 15.2% moisture sample, the error at 1 mm variation was 0.1% and at 5 mm, 0.4%. Controlling the accuracy of lens-to-detector distance to within 1 mm should be easily achieved.

Particularly for field use, a NIR meter for measuring moisture in grain which is accurate to within ±0.2% would be acceptable.

In the illustrated embodiment, the performance was aided by choosing a 1200 G/mm grating in combination with a large focal length of the focusing lens (100 mm), large detector pixel elements (5 mm by 1 mm) and a relatively large size apertures (2 mm) for the slit for the system.

This system provides a broad 13 nm per pixel spread in the spectrum, each wavelength converging on the detector at a narrow angle.

Some embodiments are specifically designed to be of a lightweight rugged construction. In one such embodiment, use is made of a housing (not shown) that contains all of the elements of instrument and which has typical overall dimensions of: length 190 mm; width 150 mm; and height 95 mm. It will be appreciated that the housing is defined by a rugged 5 mm thick PVC box. Typically collective weights of 1.7 kg have been achieved for the instrument and housing combined.

The illustrated embodiment is advantageous in that the recessed mounting apertures as shown in FIG. 1 facilitate rigid mounting of optical components which are resistant to movement under vibration. By using a material of low temperature coefficient of expansion insignificant departure from the designed optical path occurs in use.

With advantage, the detector array is mounted on an adjustment arrangement having a micrometer. To ensure that after manufacture the desired peak is centred on the centre pixel, a simple adjustment is able to be effected. In the illustrated embodiment this is achieved using a 10 nm FWHM light filter centred on the frequency of interest and this filter is inserted into the optical path. The detector output is monitored and a sharp peak value should be found on the centre pixel with an equal fractional value of the peak intensity observed on the two adjacent pixels. If necessary, the micrometer is adjusted to affect the correct physical positioning and fine-tuning of the pixels with respect to the optical path.

FIGS. 3 and 4 depict a second embodiment of the present invention wherein like elements are denoted by the corresponding reference numerals. This embodiment also comprises a base plate 10 and top plate (not shown), each about 40 mm thick and screwed together. Recesses 11, 13 and 14 are provided in both plates 8 and 10 for accommodating the optical barrel 9, reflection diffraction grating 24 and focusing lens 26.

In other embodiments alternative optical components or combinations of optical components are used to provide the same effect. For example, in one specific embodiment, the optics barrel 9 is substituted by a number of discrete components that are directly mounted to plate 10.

The sample container 15 is mounted to the base plate 10 and the light source 17 is mounted adjacent the container. Light emitted from the source passes through the sample deposited in the sample container 15, the optical barrel and then through a channel 34 between the base and top plates before reaching the reflection diffraction grating 24. The optical barrel 9; as shown in FIG. 4, contains the first convex lens 20, a circular aperture 32 and a second convex lens 33 wherein the two convex lenses 20 and 33 have equal focal lengths and are equally displaced from the aperture 32. The first lens 20 focuses the light beam through the aperture 32 which removes light noise and then the second lens 33 makes the beam parallel again. This process converts scattered light into a parallel light beam. The light is then incident at an angle to the grating which splits the beam into a plurality of diverging beams 35, each beam representing a particular frequency of light. This plurality of beams then passes through a focusing lens 26 which focuses them onto the detector 28.

In this embodiment, each pixel of the detector 28 array will detect a narrow band of about 5.5 nm. The grating will need to be mounted at 17° for moisture detection and at this angle, light of a wavelength of 485 nm will have a second order diffraction angle equal to 17°. In this embodiment it was found that the distance from the focusing lens 26 to the detector could be 75 mm (±5 mm) without significant degradation of performance. So this system provides a narrow 5.5 nm per pixel spread in the spectrum.

To ensure that after manufacture the desired peak: is centred on the centre pixel, three light filters centred on the frequency of interest may be inserted into the optical path and simple adjustments based on the outcome can then be made.

The detector array can also be mounted on an adjusted arrangement having a micrometer adjustment to facilitate appropriate positioning after assembly.

Figure 5:
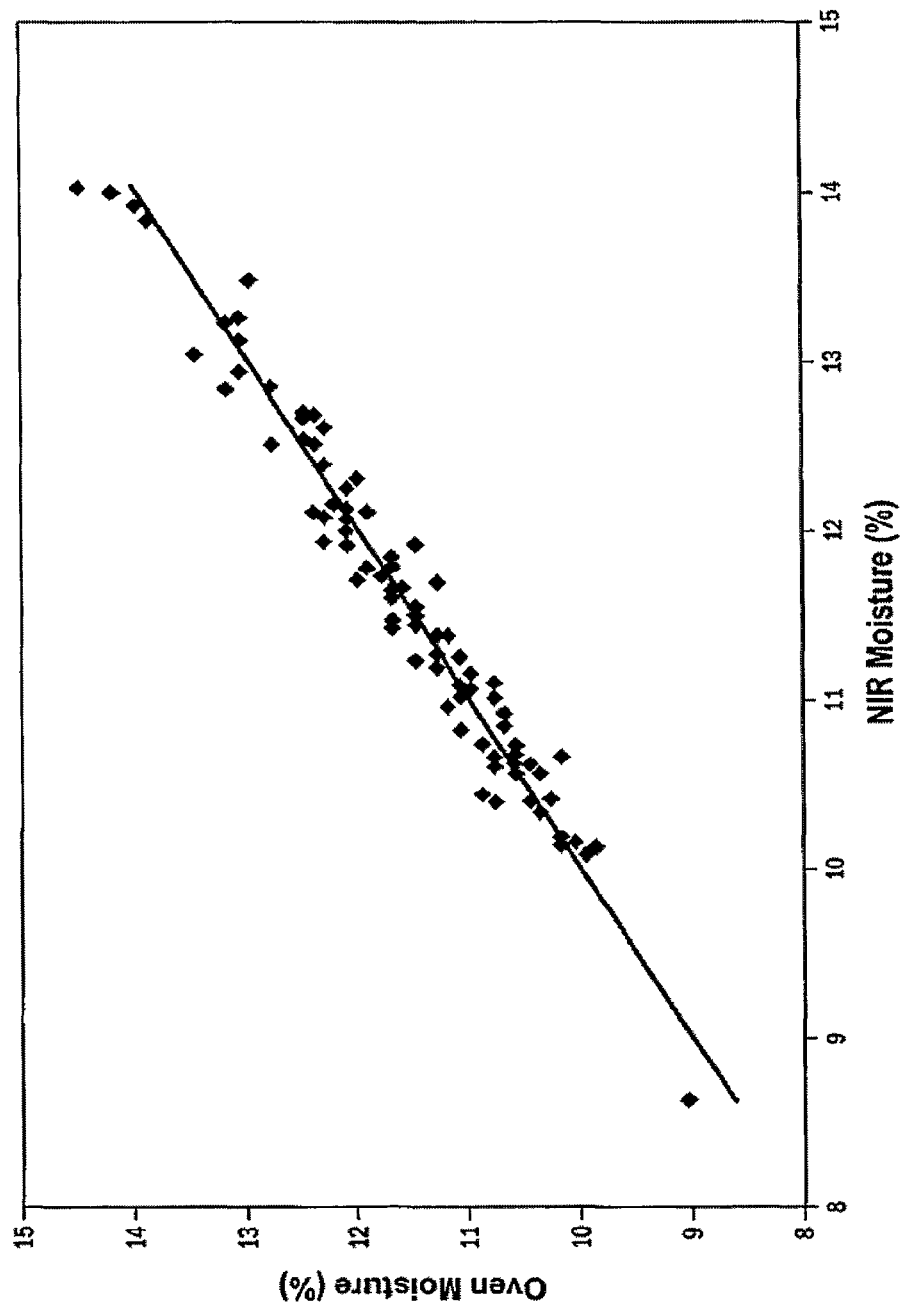
FIG. 5 is a graph showing the relationship between wheat moisture levels against calibration samples laboratory measured by oven techniques, showing a line of best fit and validating effective use of the present embodiment across the important range of around 10% to 14% moisture for wheat.

Detailed description will now be given of FIGS. 5 to 7. Referring first to FIG. 5, a plot is made of numerous experiments using an embodiment wherein the moisture, as determined by the embodiment, is the NIR moisture and is plotted with reference to the moisture calibration samples as accurately determined in a laboratory using an oven drying technique. A line of best fit is shown on the diagram and is considered to validate with an acceptable tolerance the data across the range of moisture. Additional experiments have confirmed that valid data can be obtained for wheat across a range of around 7% to 17% moisture which covers all practically significant values.

Set out below are tables for 10 sample wheats providing specific data at particular moisture levels.

|    | Laboratory Measured Moisture (%) | NIR Predicted Moisture (%) | Difference (%) |
|----|----------------------------------|----------------------------|----------------|
| 1  | 9.7                              | 9.7                        | 0.0            |
| 2  | 10.1                             | 10.0                       | 0.1            |
| 3  | 11.0                             | 11.1                       | −0.1           |
| 4  | 12.0                             | 12.0                       | 0.0            |
| 5  | 12.2                             | 12.3                       | −0.1           |
| 6  | 13.3                             | 13.4                       | −0.1           |
| 7  | 13.6                             | 13.6                       | 0.0            |
| 8  | 14.3                             | 14.2                       | 0.1            |
| 9  | 15.0                             | 14.8                       | 0.2            |
| 10 | 15.7                             | 15.6                       | 0.1            |

Figure 6:
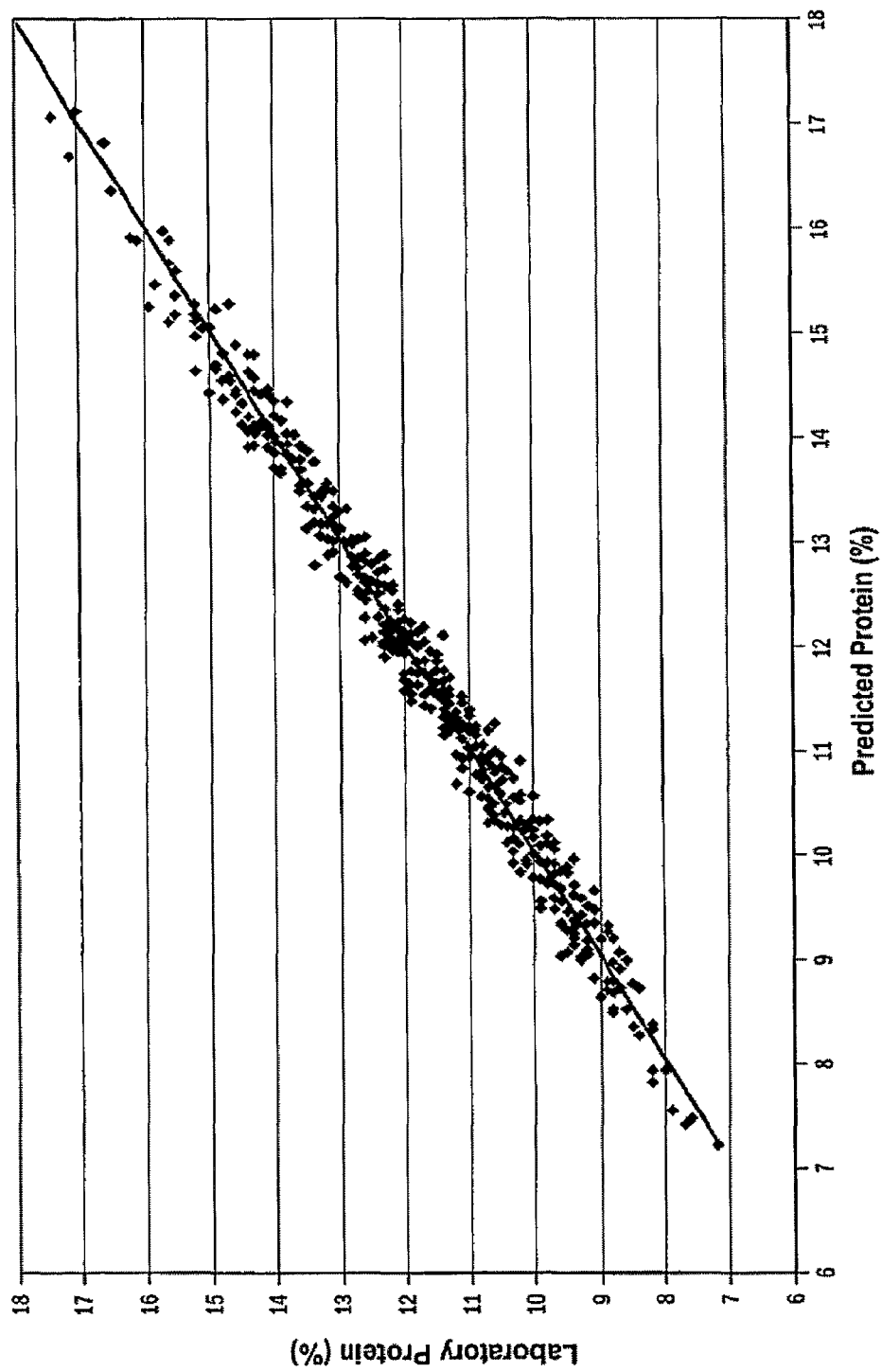
FIG. 6 is a graph validating protein levels in wheat in the range 7% to 17% performance of an embodiment.

Referring to FIG. 6, a plot shows close correlation between protein content determined by laboratory measurements against values determined by use of an embodiment of the invention. Set out below is a table of specific data for 10 different wheat samples.

|    | Laboratory Measured Protein (%) | NIR Predicted Protein (%) | Difference (%) |
|----|----------------------------------|---------------------------|----------------|
| 1  | 12.6                             | 12.5                      | 0.1            |
| 2  | 13.2                             | 13.5                      | −0.3           |
| 3  | 11.4                             | 11.5                      | −0.1           |
| 4  | 16.1                             | 15.8                      | 0.3            |
| 5  | 11.1                             | 11.1                      | 0.0            |
| 6  | 13.4                             | 13.2                      | 0.2            |
| 7  | 9.8                              | 9.9                       | −0.1           |
| 8  | 12.9                             | 13.0                      | −0.1           |
| 9  | 10.4                             | 10.7                      | −0.3           |
| 10 | 8.4                              | 8.3                       | 0.1            |

Referring now to FIG. 6, a graph of absorption of three typical wheat samples is shown. The absorption scale is the logarithm of the ratio of background to sample and thus a high absorption wheat sample has a high ratio of background to sample and is the uppermost trace. This contrasts with the lower absorption wheat on the lower-most trace. The diagram takes the values of absorption across 38 pixels which presents a range of segments of the NIR spectrum to cover the area of interest. Broadly it follows that a high absorption wheat will require a longer integration time to bring the pixel values up to the desired range of about 60% to 80% of maximum and for a low absorption, that is high transmittance wheat the system means to ensure that there is no saturation at any pixels and integration time may need to be reduced.

A typical embodiment will use a 20-bit amplifier so a signal value of between 0 and 1,048,576 can be read. The target for operational optimisation is 60% to 80% of this range. Auto-ranging is thus used to obtain maximum electronic resolution and therefore accuracy in the results.

The absorbency of each individual pixel is calculated using the appropriate correction factor for each pixel which is the ratio of sample integration time to background integration time that is integration time that is appropriate with no sample in place. The absorption is given by the formula:

$$A = \log\left(\frac{B}{S} \times C\right)$$

where:
A=absorption;
B=background radiation;
S=sample radiation; and
C=correction factor.

Figure 7:
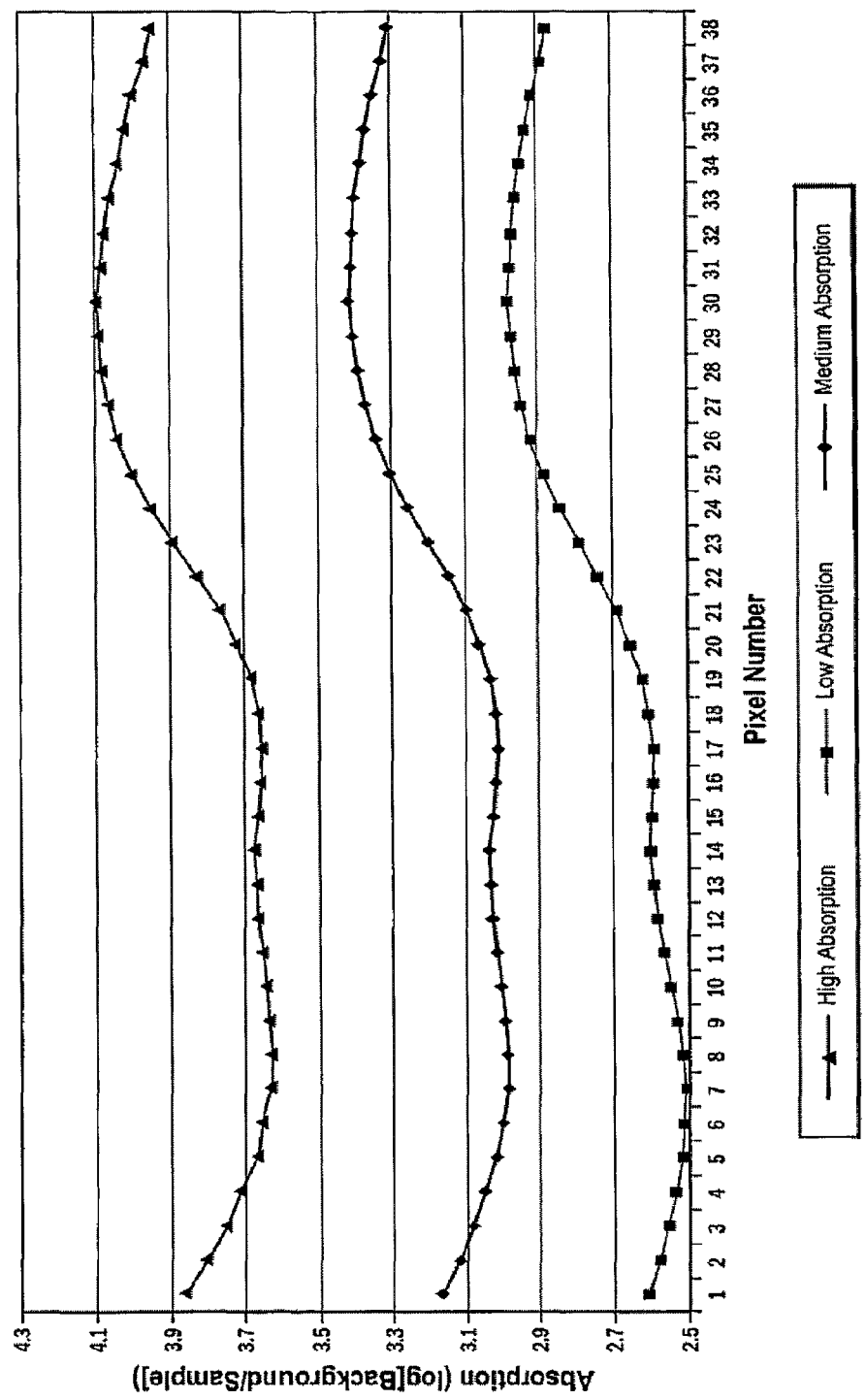
FIG. 7 comprises graphs indicating tests across a 38 pixel embodiment showing relative absorptions of light for three different wheat samples.
Figure 8:
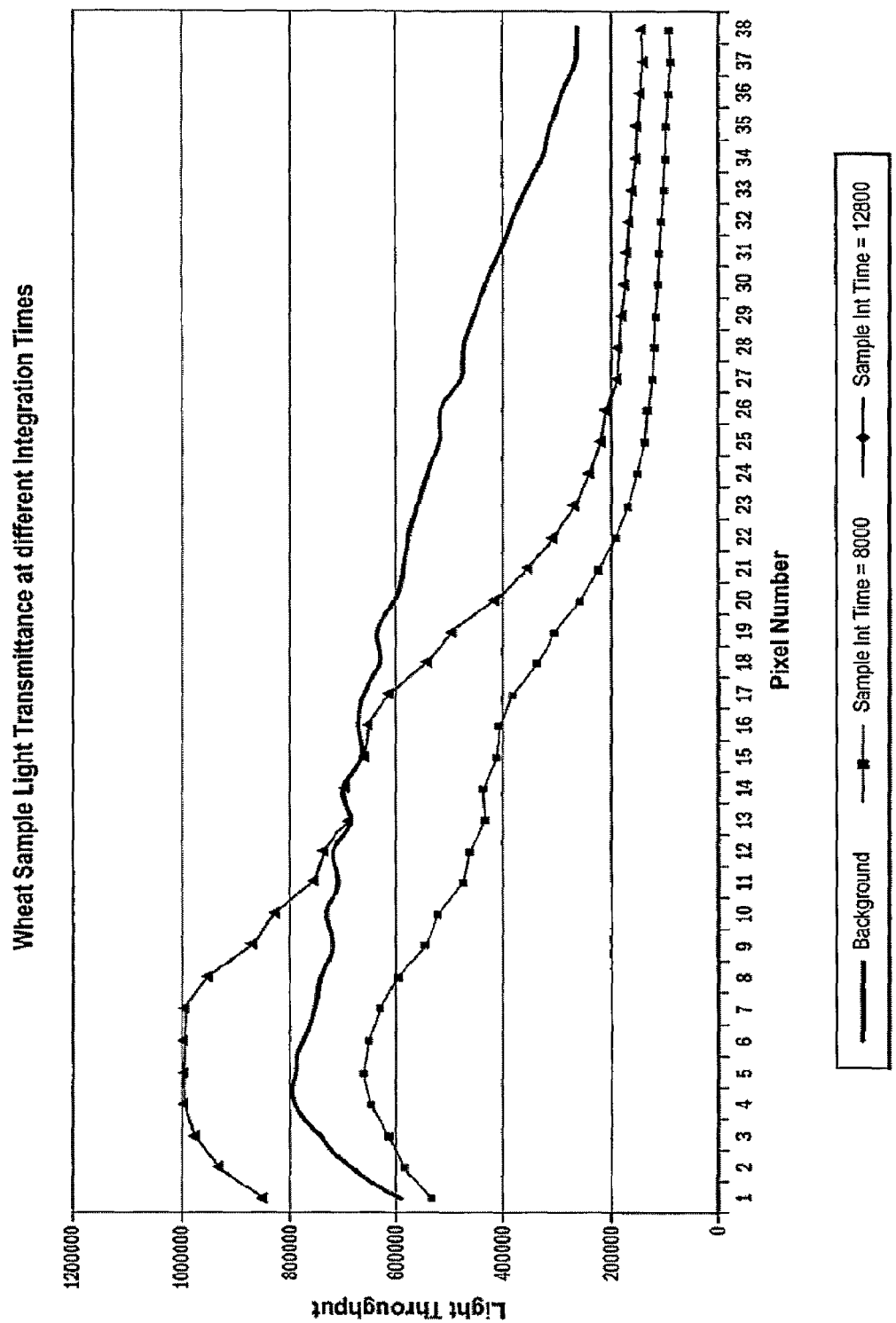
FIG. 8 is a graph illustrating wheat sample-light transmittance at different integration times across a 38 pixel model.

Referring now to FIG. 7, a plot is made of the level of light transmittance through a wheat sample at two different integration times. At an integration time of 8,000 μs none of the 38 detector pixels saturate whereas at an integration time of 12,800 μs four pixels are saturated by the level of light incident on them. The background level of light is also shown.

Figure 9:
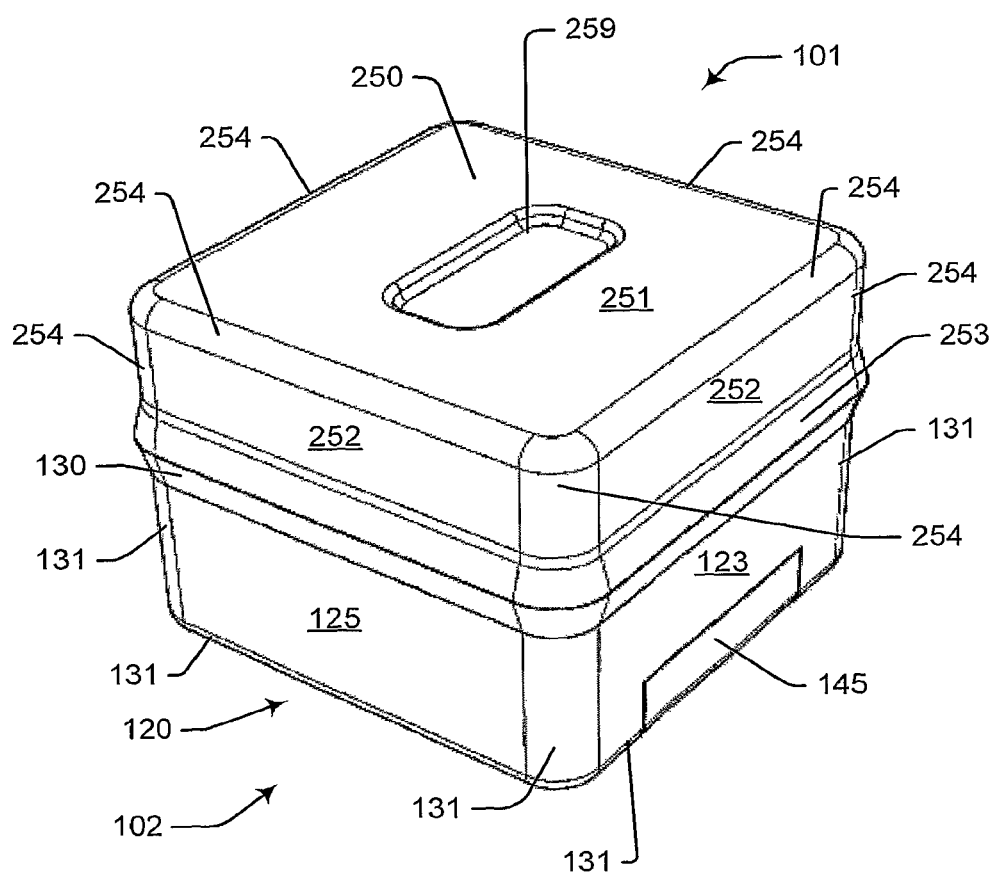
FIG. 9 is a perspective view of an embodiment of a field-use optical grain characterising system in a closed configuration.
Figure 10:
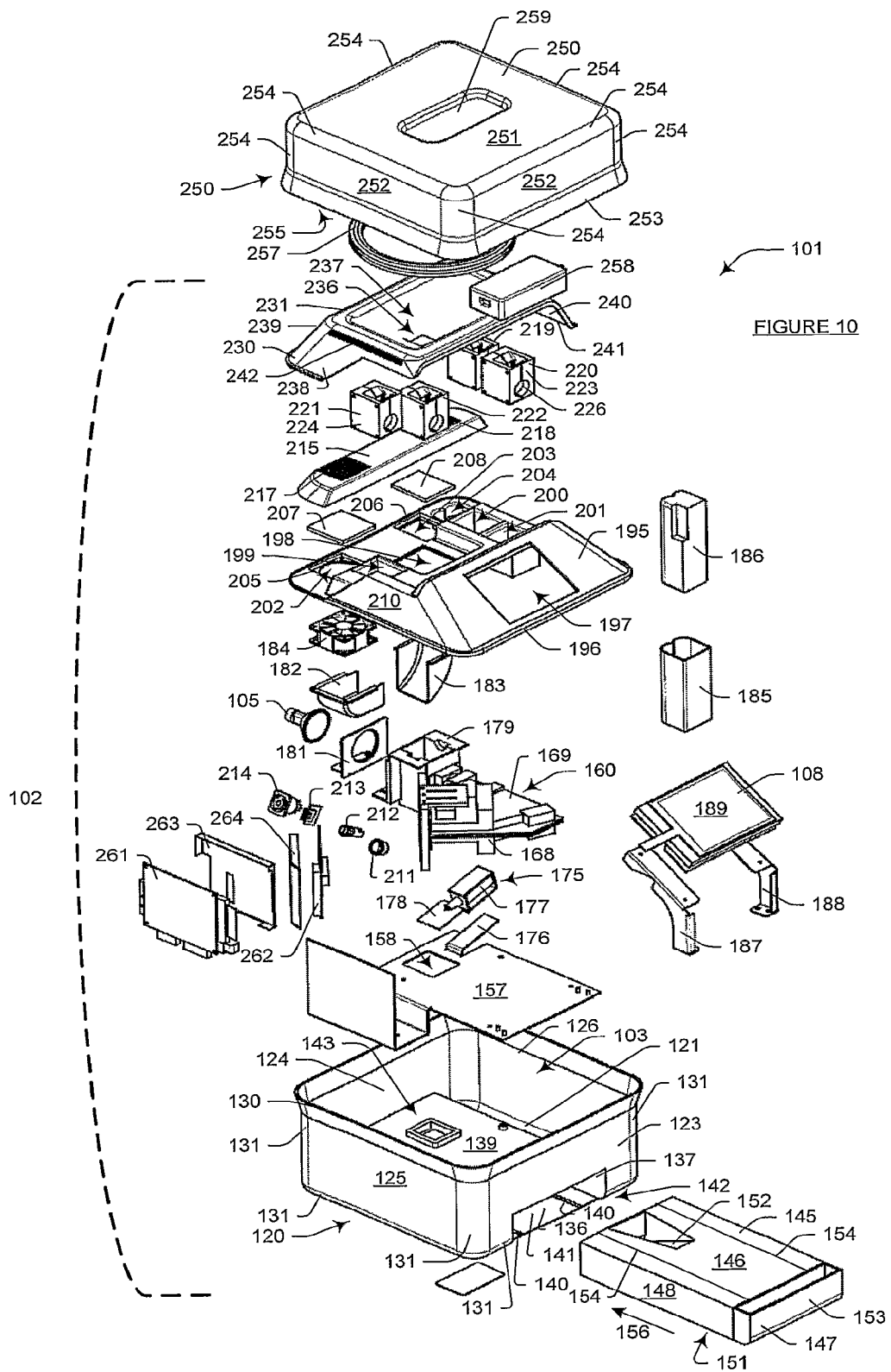
FIG. 10 is an exploded view of the system of FIG. 9.
Figure 17:
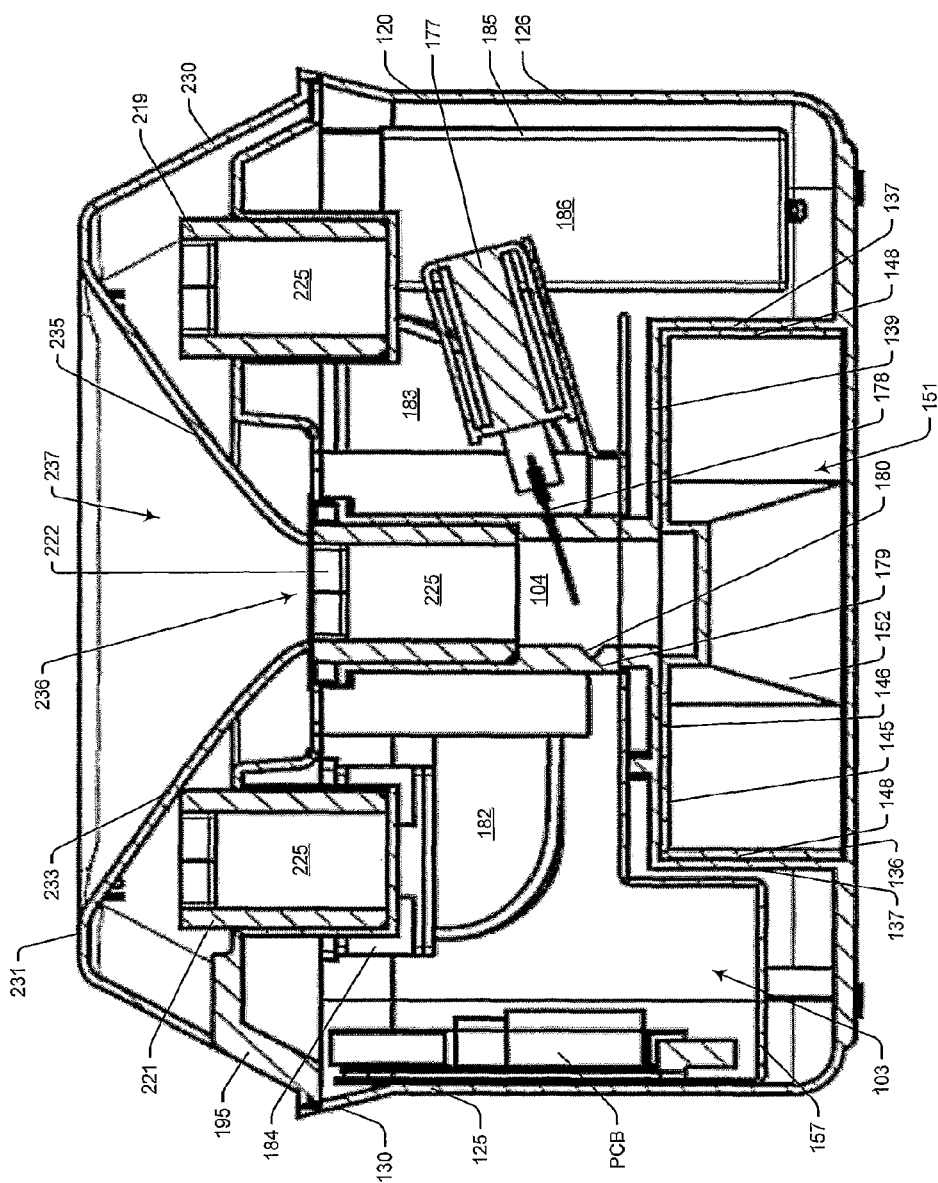
FIG. 17 is a cross-sectional view taken on line 17-17 of FIG. 15.
Figure 18:
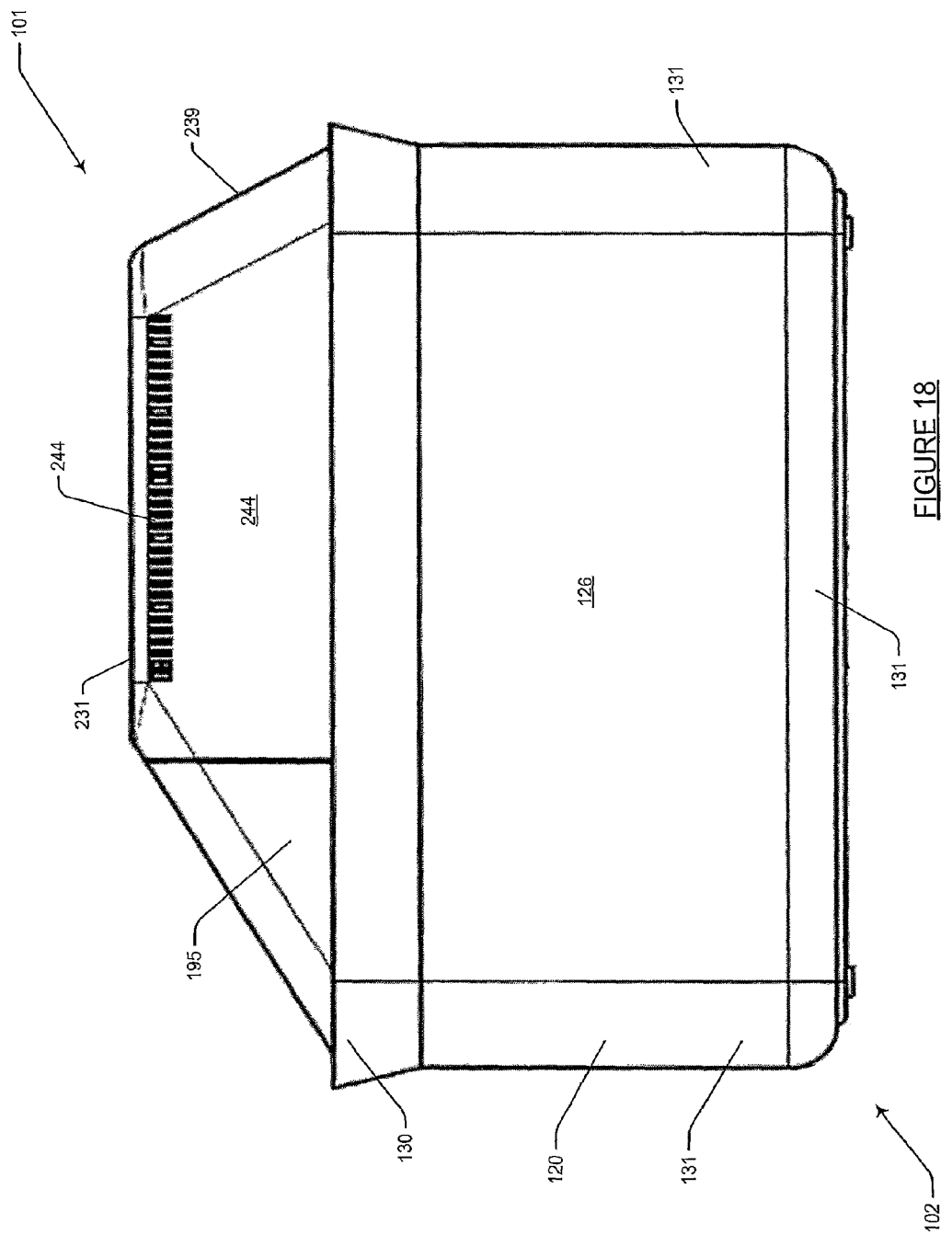
FIG. 18 is a side view of the system of FIG. 11.
Figure 19:
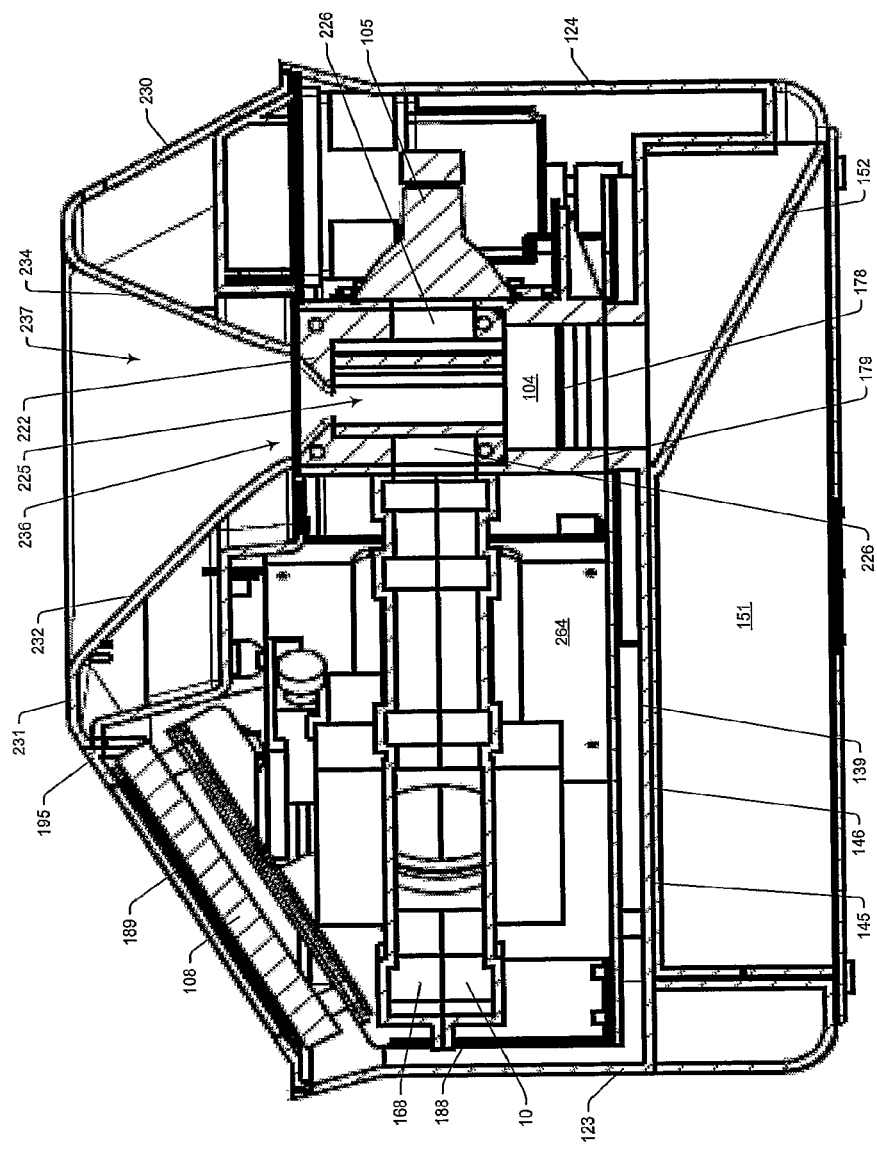
FIG. 19 is a cross-sectional view taken on line 19-19 of FIG. 15.

Another embodiment of the invention is illustrated in FIGS. 9 to 20 Particularly, referring to FIGS. 10, 17 and 19 there is shown a field use optical grain characterising system 101 which includes a generally rectangular prismatic composite body 102 that defines a component cavity 103. A substantially vertical elongate channel 104 extends within cavity 103 for housing a grain sample (not shown). An electromagnetic radiation source, in the form of a 12 Volt halogen lamp 105, is disposed within cavity 103 for directing NIR light into channel 04. An optical detection system 107 is disposed within cavity 103 for sensing selected light emerging from channel 104 and for providing a sensor signal. A processor, which is included within detection system 107, is also disposed within cavity 103 and is responsive to the sensor signal for providing data indicative of a characteristic parameter of the grain sample. A display device, in the form of a 5.7-inch touch screen LCD display 108, is connected with body 102 for selectively presenting the data.

Body 102 includes a plastics base unit 120 having a generally horizontal floor element 121. A transverse front wall 123 and rear wall 124 extend upwardly from element 121, where wall 124 is longitudinally spaced from and parallel to wall 123. Base unit 120 further includes a pair of opposed substantially symmetric longitudinal and transversely spaced apart substantially parallel sidewalls 125 and 126 that extend upwardly from element 121. These sidewalls also extend longitudinally between wall 123 and 124. Element 121, walls 123 and 124, and sidewalls 125 and 126 are integrally formed and partially define cavity 103. Moreover, walls 123 and 124, and sidewalls 125 and 126 terminate in a continuous integrally formed outwardly flared flange 130.

In this embodiment the intersection of walls 123 and 124 with adjacent sidewalls 125 and 126, and the intersection of the walls and sidewalls with element 121 takes the form of rounded corners 131. These corners, and particularly those between walls 123 and 124 and sidewalls 125 and 126, have a significant curvature—a radius of about 10% of one side or 34 mm in this embodiment—to contribute to the robustness and strength of body 102, and to reduce the risk of the body inadvertently catching or snagging adjacent objects.

In this embodiment, cavity 103 is generally shaped as a rectangular prism. In other embodiments, cavity 103 is an alternative three-dimensional shape such as a cylinder. In further embodiments, cavity 103 is asymmetric.

Walls 123 and 124 and sidewalls 125 and 126 are generally planar and of substantially uniform thickness. However, in other embodiments the thickness varies and/or one or more of the walls and sidewalls are curved.

Body 102 in general, and base unit 120 in particular, are moulded from relatively hard plastics material and have a high strength and good scratch resistance.

Element 121 includes a floor 136 and a pair of longitudinally extending generally parallel transversely spaced apart sidewalls 137 that are mounted to floor 136 and which support a drawer roof 139. Floor 136 includes a pair of longitudinally extending parallel guide rails 140 on an upper surface 141 of floor 136 parallel to and intermediate sidewalls 137. Floor 136, sidewalls 137, and roof 139 collectively define a substantially rectangular prismatic open-ended drawer recess 142. The recess extends longitudinally between wall 123 and wall 124. Roof 139 includes an aperture 143 that is disposed centrally transversely within cavity 103 and adjacent to wall 124 for defining a lower end 144 of channel 104.

A collection drawer 145 is complementarily received within in recess 142 selectively in one of two orientations. Drawer 145 includes a base 146, four sidewalls 147, 148, 149 and 150 that extend normally from base 146 to define a sample receiving receptacle 151. Drawer 145 also includes a guide formation in the form of an inclined ramp 152 that extends from sidewall 149 to base 146 for selectively directing the grain sample. This function will be described in more detail below.

Sidewall 147 includes a fascia 153 to facilitate manual handling of drawer 145. There are provided a two pairs of complementary parallel guide rail engaging formations 154 and 155 corresponding to guide rails 140 to maintain drawer 145 in correct alignment with recess 142.

Figure 11:
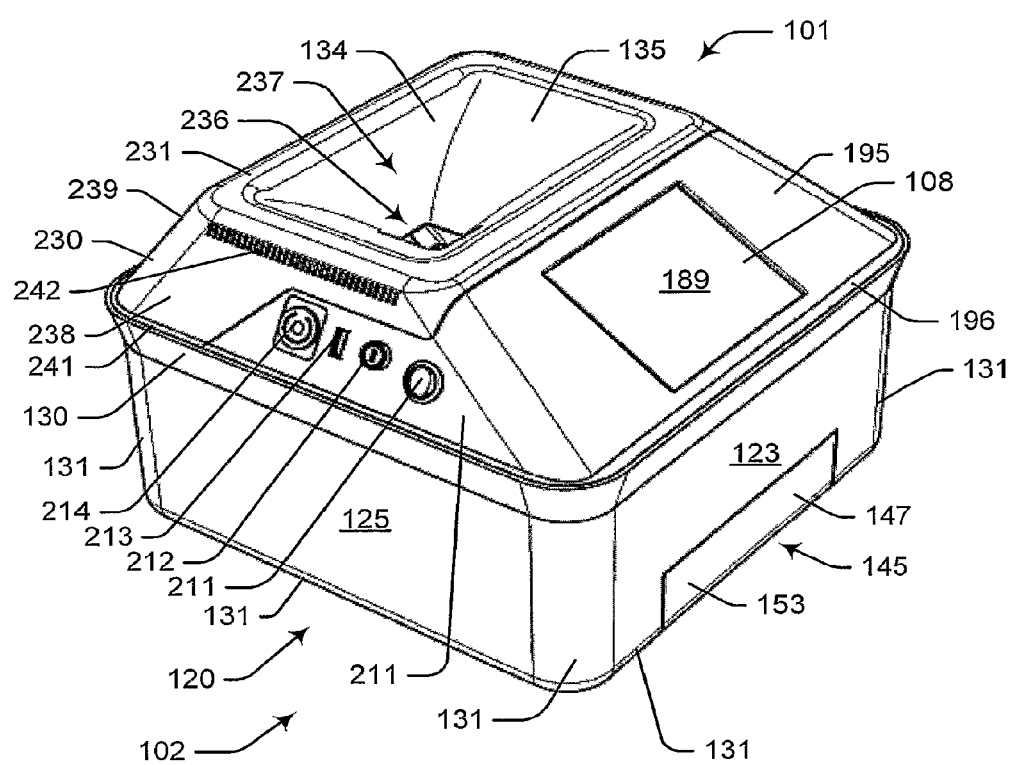
FIG. 11 is the system of FIG. 9 with the lid removed from the body.

Drawer 145 is illustrated in FIG. 10 in a first orientation where base 146 is uppermost, and receptacle 151 is downwardly opening. Drawer 145 is progressed in the direction of arrow 156 such that sidewall 149 is first received within recess 142. The progression is continued until all of drawer 145 is entirely complementarily nested within recess 142, and with fascia 153 being flush with wall 123, as best shown in FIG. 11. Drawer 145 is secured in the closed position by an interference fit between rails 140 and fascia 153. In other embodiments use is made of an alternative locking mechanism, such as a snap lock or clip (not shown). In the second orientation (not shown) drawer 145 has the base lowermost, and receptacle 151 upwardly opening. In the second configuration the sample, upon emerging from channel 104, is diverted toward wall 124 and allowed to fall to the surface underlying system 101.

The volume of drawer 145 is approximately 420 ml and the volume of receptacle 151 is about 400 ml. It will be appreciated that in alternate embodiments the volume of drawer 145 is more or less than 420 ml.

In this embodiment about twelve measurements are taken for each sample across a range of grains in the sample. More particularly, the sample is progressed through channel 104 in twelve discrete increments of about 30 ml, where each increment is subject to a separate measurement to provide a set of measurements. That is, the sample signal is comprised of the twelve measurements, and the processor is responsive to these measurements for providing the data. In this embodiment two of the twelve measurements in the set of measurements for a sample are discarded, and the remainder averaged to provide the data. As the volume of each increment of the sample is about 30 ml, all twelve samples are able to be held with the receptacle. That is, the volume of receptacle 151 is greater than or equal to the likely volume of the sample required to provide the data. In this way, drawer 145 need only be emptied following the data being provided. In other embodiments the volume of receptacle 151 is greater than the combined volume of all the increments to be measured. In further embodiments, drawer 145 is omitted and the sample, after exiting channel 104, falls downwardly under the influence of gravity onto the surface below system 101.

In other embodiments drawer 145 includes a load sensor for providing an indication that drawer 145 is full or nearly full of grain from the sample or subsequent samples. The processor is responsive to the indication for preventing further operation of system 101 and for providing an alert signal to encourage the emptying of drawer 145.

Body 102 includes a punched metal chassis 157 that is disposed within cavity 103 adjacent to base unit 120. In this embodiment chassis 157 is releasably mounted by screws to roof 139 and sidewall 125. In other embodiments, alternative fasteners are used and the chassis is fixed to additional or alternative walls or sidewalls of body 102. In still further embodiments, chassis 157 is fixedly mounted to one or more other parts of body 102.

Chassis 157 includes a generally square aperture 158 that, in use, overlies and surrounds aperture 143.

Chassis 157 is adapted to support the specific components of this embodiment.

Figure 21:
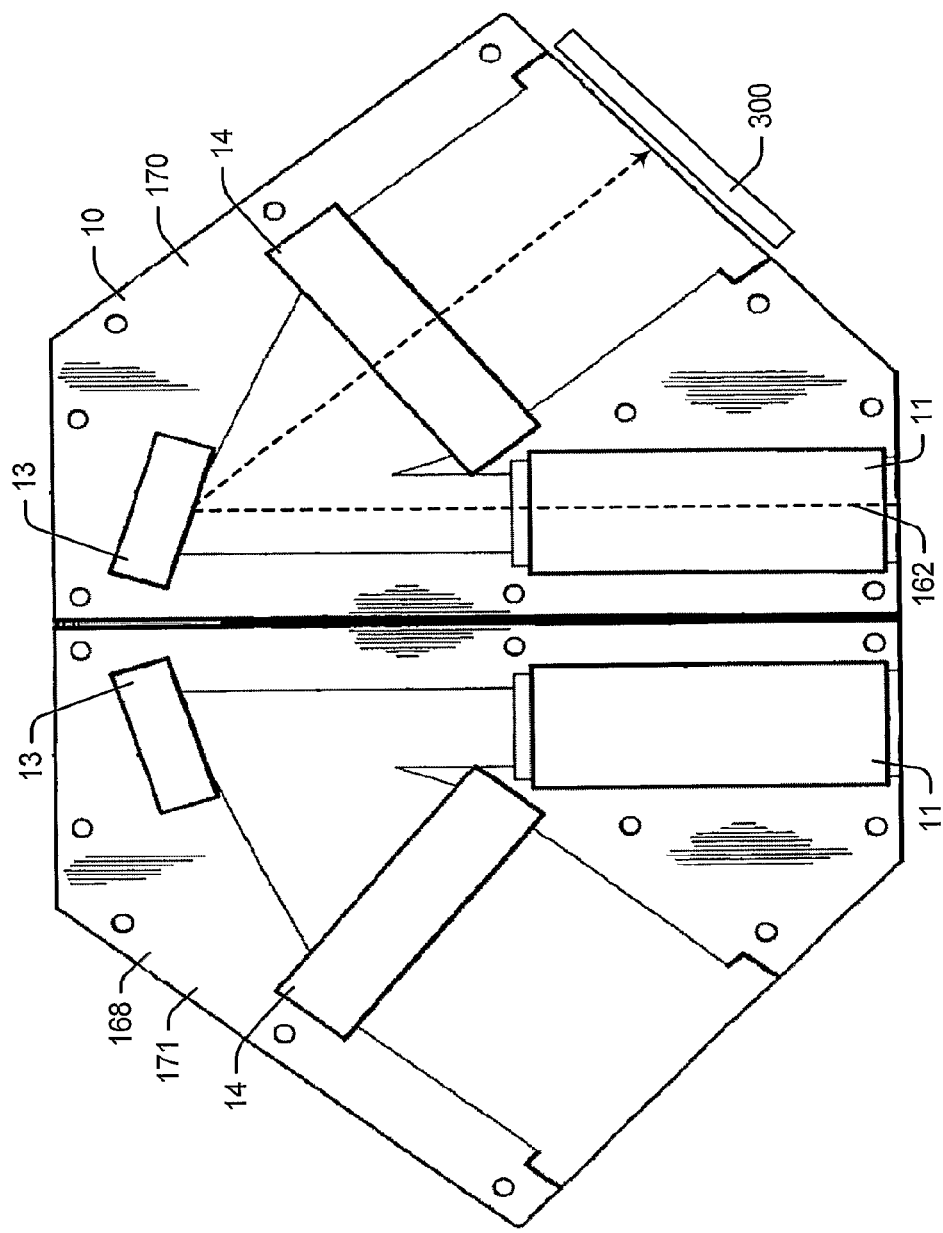
FIG. 21 is the plate of FIG. 3 shown adjacent a corresponding top plate.
Figure 22:
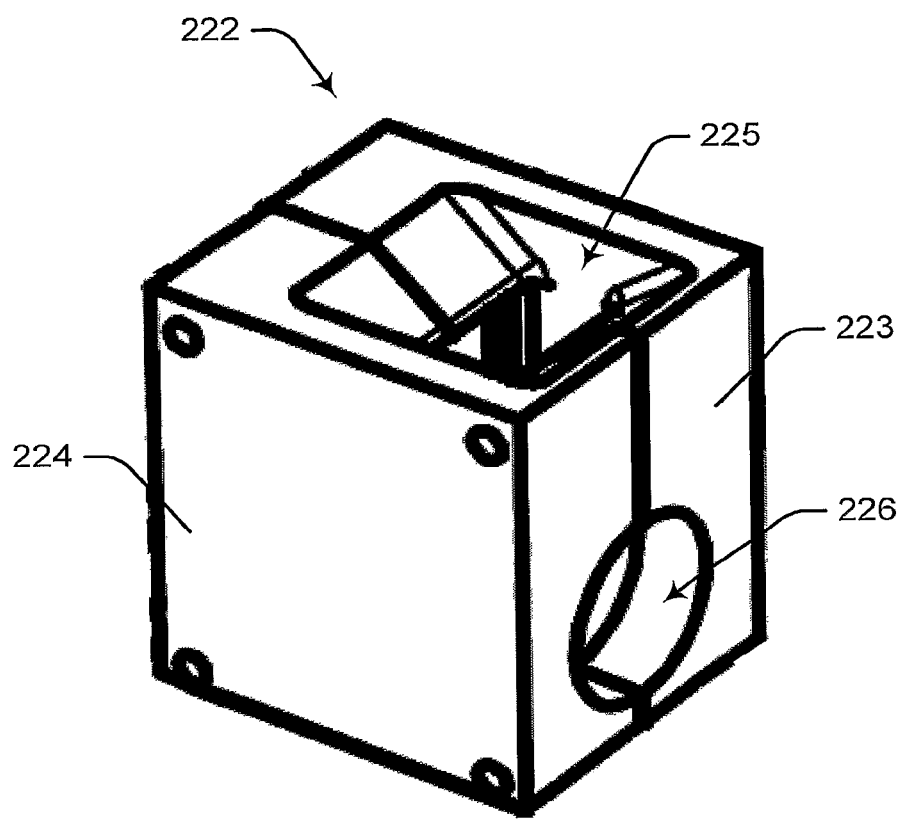
FIG. 22 is an enlarged perspective view of one of the cartridges of FIG. 10.

Referring again to FIG. 10, system 107 includes a rigid base plate 160 having corresponding features denoted by corresponding reference numerals. As best shown in FIG. 21, plate 160 defines multi-segment optical path 162. Base plate 160 includes mounting plate 10 for partially defining formations 11, 13 and 14 and a top plate 168 substantially mirroring mounting plate 168 for defining the remainder of the formations. Plates 10 and 169 include respective sealing faces 170 and 171 that, in use, are opposed and abutted to sealingly engage with each other, as best shown in FIG. 19. Plates 10 and 168 collectively define an optics cavity 172 for containing barrel 9, grating 24 and lens 26. Barrel 9 and lens 26 are sealingly received by respective formations 11 and 14 to impede the ingress into cavity 172 of dust and other contaminants. In other embodiments only lens 26 is sealingly received by formation 14.

In some embodiments faces 170 and 171 includes opposed channels (not show) for collectively receiving a continuous sealing bead (not shown) that is, in use, clampingly retained between the faces to further enhance the sealing between those faces. In other embodiments use is made of a plurality of discrete beads.

In other embodiments plate 160 includes other than three formations and/or differently shaped formations for complementarily receiving different numbers and/or shapes of components. For example, FIG. 1 illustrates an embodiment with four formations for respectively complementarily receiving four specific components.

Plate 160 is releasably mounted directly to chassis 157 for ease of servicing or replacement.

Plate 160 is injection moulded from CYCOLOY XCM850, but in other embodiments alternative materials are used. Some examples of these materials are provided in the following table, together with selected properties of those materials.

|  | Cycoloy XCM850 | Cycoloy XCM830 | Valox 365 | Delrin Acetal | TR-Acetal |
|---|---|---|---|---|---|
| Continuous Heat Deflection @>115° C. (3.2 MM) | 121° C. | 120° C. | 121° C. | 125° C. | 121° C. |
| Dimensional Stability (Injection Moulding) | Great | Good | Good | Good | Good |
| CTE m$^{-5}$/m/° C. | 4.30 | 6.00 | 6.84 | 10.4 | 8.46 |
| Good Impact (instrumented) | 60 J | 65 J | 37 J | Not available | Not available |
| Izod notched 23° C. J/m | 170 | 500 | 640 | 80 to 123 | 53 |
| Rigidity (modulus - Mpa) | (2 mm) 4450 | (2 mm) 3000 | (1.3 mm) 2240 | (1.3 mm) 2900 | (1.3 mm) 3102 |
| Water Absorption | 0.20% | 0.40% | 0.14% | 0.25% | 0.20% |

It will be appreciated by those skilled in the art that the following points apply for the above table:
  The "Good Impact" is a standardised test with the full title of "Instrumented Impact Total Energy @23° C.". The Australian Standard for this test is Test Standard ASTM D 3763.
  The "Izod notched" is a standardised test otherwise known as the Notched impact strength test. The standard test procedure is described in Australian Standard ASTM D 256.
  The reference to 1.3 mm and 2 mm in the row marked "Rigidity" refer to the test speed (being 1.3 mm/min and 2 mm/min respectively). The test for rigidity is carried out under an Australian Standard for testing No. ASTM D 790.
  In the row marked "Water Absorption", the percentage figures refer to the saturation percentage water absorbed by weight at 20° C. and 50% RH. For example, 0.2% means that a 1 kg piece of the relevant material at saturation equilibrium will contain 2 grams of moisture at air temperature 20° C. and at 50% RH.

Base plate 160 advantageously has one or a combination of:
  A high continuous heat deflection, and preferably greater than 115° C.
  High intermittent working temperature, preferably greater than 140° C. as measured in accordance with Australian Standard test D648.
  At least good dimensional stability following injection moulding.
  A low Coefficient of Thermal Expansion (CTE) which is preferable less than about 12 m$^{-5}$/m/° C., and more preferably less than about 9 m$^{-5}$/m/° C.
  Good Impact (instrumented) rating of greater than about 30 J.
  Izod notched rating of at least 40 J/m.
  High rigidity, and preferably with a rigidity (modulus) of greater than 2,000 MPa.
  Water Absorption of less than 0.5%.
  Other advantageous properties of the selected material are a high working temperature and a high resistance to warping due to heat.

Importantly, in this embodiment, plate 10 and plate 168 are both injection moulded to normal engineering tolerances. This allows for the cost effective manufacture of the plate.

While these tolerances will have some effect on the relative placement of the optical components, it has been found, perhaps counter-intuitively, that these tolerances do not compromise the optical path within base plate 160 so long as a single adjustment is possible. In this embodiment, that adjustment is a one-off initial lateral adjustment of an IC sensor 300 relative to the light emerging from the path. Accordingly, that adjustment is able to be made at the time of manufacture and generally need not occur again during the normal operating lifetime of system 101.

The high rigidity and stability of the material selected to form base plate 160, together with the good impact properties, allow system 101 to provide accurate field based characterisation of the samples over a useful lifetime in the field.

Referring back to FIG. 10, chassis 157 includes an inclined mounting formation 176 that extends upwardly and away from aperture 158 and toward sidewall 126. A sample flow controller, in the form of a metal gate assembly 175 is fixedly mounted to the formation 176 for selectively extending across channel 104 adjacent to aperture 143. Assembly 175 includes a drive device, in the form of a low voltage DC solenoid 177, that is responsive to a drive signal to progress between an extended and a retracted state. A barrier formation, in the form of a blade 178, is operatively attached to solenoid 177 for moving away from and toward the solenoid in response to progression to the extended and the retracted state respectively. When solenoid 177 is in the extended state, blade 178 spans channel 104 to effectively prevent further progress of the sample through the channel and toward aperture 143. That is, blade 178 is selectively maintained within channel 104 as a barrier to the flow of the sample through the channel. When solenoid 177 is in the retracted state, blade 178 does riot span channel 104, and the sample is able to progress through channel 104. It is not necessary for blade 178, when the solenoid is in the extended state, to be totally withdrawn from channel 104. In this embodiment blade 178 is only partially withdrawn to allow a predetermined rate of flow of the sample through channel 104 under the influence of gravity.

By way of example, for a sample of wheat grains, it has been found that for the channel cross-sectional area, that solenoid 177 is switched to the retracted state for 700 msec to allow an incremental flow for the sample of 30 ml. This volume corresponds to the increments of the sample referred to above. It will be appreciated by those skilled in the art, given the benefit of the teaching herein, that the time solenoid 177 is switched to the retracted state will vary due many factors, including: the flow properties of the grain in the sample; the volume of the increment; and the cross-section of the channel. Accordingly, for a sample of a smaller grain such as canola which has greater rates of flow—and assuming the same channel cross-section and volume increment—the switching time will be less.

Due to the inclination of formation 176, blade 178 is inclined at about 14° from the horizontal to improve the barrier properties provided by blade 178 to the flow of the sample and, in particular, to reduce the risk of the blade fouling with the sample. It has been found that improved barrier properties are gained when blade 178 is inclined from the horizontal by between about 10° to 30°. In other embodiments inclinations outside that range are used.

It will be appreciated that, in this embodiment, the sample flows substantially vertically downwardly through channel 104 under the influence of gravity. Accordingly, blade 178 is inclined at about 76° to the direction of the flow. It has been found that improved barrier properties are gained when blade 178 is inclined from the direction of the flow by between about 60° to 80°.

Body 102 includes an elongate sample well 179 that is disposed adjacent to plate 160 for defining a lower portion of channel 104. As best shown in FIG. 17, well 179 includes a blade receiving notch 180 for receiving blade 178 when in the extended state. This further improves the barrier properties provided by blade 178 to the flow of the sample through channel 104. Notch 180 extends laterally across the channel and includes two inclined surfaces, the first for remaining spaced apart from the distal end of blade 178, and the other for slideably engaging with the upper surface of blade 178 adjacent to that distal end. If, as blade 178 is about to be received within notch 180, there are any grains in contact with the distal end of the blade, those grains will progress into notch 180 and continue to fall downwardly within channel 104. That is, in the absence of notch 104 there is a greater risk that any grains in contact with the distal end of blade 178 will become trapped between that distal end and the adjacent wall of well 179 and, hence prevent blade 178 from completely spanning the channel and blocking the flow of the sample.

There is also provided a plurality of brushes (not shown) to clean solenoid 177. These brushes are conveniently storable within cavity 255.

It will be appreciated that in other embodiments assembly 175 includes an alternative drive device and/or an alternative barrier formation. For example, in one embodiment barrier formation is a butterfly valve.

Lamp 105 is mounted complementarily to a punched metal mounting bracket 181. In turn, bracket 181 is fixedly mounted to chassis 157 adjacent to aperture 158. In alternate embodiments bracket 181 is integrally formed with chassis 157. In further alternate embodiments lamp 105 is other than a 12 Volt halogen lamp, and in yet further embodiments is a source of other than NIR electromagnetic radiation. For example, in some embodiments the source provides one or more of: visible radiation; infrared radiation; and ultraviolet radiation.

Display 108 is fixedly mounted to a pair of metal mounting brackets 187 and 188. Brackets 187 and 188 are, in turn, mounted to chassis 157. Display 108 is shielded by an outer substantially planar protective layer 189 formed from a substantially robust transparent material. Layer 189 is disposed immediately adjacent to display 108 and functions to protect display 108 from damage such as scratching or breakage.

Display 108 is mounted at a predetermined angle of about 28° from the horizontal for ease of viewing and to minimise the glare from the surrounding environment. It will be appreciated that in other embodiments, display 108 is mounted at an angle greater or less than 28° from the horizontal. Display 108 is a colour screen, but in other embodiments alternative screens such as a black and white screen or a monochrome screen are used.

In some embodiments layer 189 extends beyond display 108 to also shield other components that are to be available for viewing. For example, in one embodiment the components include indicia such as:

Safety warning messages for operators of system 101.
Instructions for use of system 101.
A company's insignia or logo.

This allows the indicia to remain generally undamaged and visible for longer periods of time than would have otherwise occurred.

In further embodiments display 108 includes a paper printer (not shown) that selectively presents the data in a printed form. In yet further embodiments the display 108 includes an audio amplifier and speaker for selectively audible presenting the data.

In some embodiments display device 108 is releasably mounted to the body 102. An alternate embodiment has the display device selectively or permanently physically separated from the body connected wirelessly with the body and, more particularly, with detection system 107.

Screen 108 and drawer 145 are accessed from front surface 123 and system 101 is left-to-right symmetric. Tins allows for ease of use for both right handed and left handed operators.

Body 102 includes a hard plastics cover 195 having a generally square periphery 196 that is sealingly nestingly received within flange 130, in that periphery 196, in use, lies vertically below an uppermost edge of flange 130. Cover 195 includes a plurality of apertures including:

A generally rectangular inclined aperture for defining an access window 197 for overlying screen 108.

A generally square aperture 198 for defining an upper end 206 of channel 104.

Three generally rectangular prismatic upwardly opening receptacles 199,200 and 201.

A generally circular aperture for defining an inlet 202 for an air intake duct 182.

A generally square aperture defining all outlet 203 for an air exhaust duct 183.

An aperture 204 for receiving an elongate battery receptacle 185.

Inlet 202 and outlet 203 respectively include inwardly extending flanges 205 and 206. Two substantially planar air filters 207 and 208 are respectively received within inlet 202 and outlet 203 and rest against respective flanges 205 and 206.

As best shown in FIG. 11, cover 195 includes an integrally formed substantially planar mounting surface 210 for supporting:

A depressible two-state activation switch 211 for selectively progressing system 101 between an ON state and an OFF state.

A fuse 212.

An electronic communications port, in the form of a USB port 213 for allowing system 101 to communicate with a remote computer or computer network.

An external power source connection point in the form of a cigarette lighter socket 214.

In other embodiments additional or alternative ports and components are used. For example, in some specific embodiments cover 195 includes a memory device port for receiving one or more memory devices such as SD cards, USB flash drives, Compact Flash cards, xD cards, or other memory storage media.

Referring again to FIG. 10, receptacle 185 complimentary houses a power source in the form of a 12 Volt rechargeable lithium ion battery pack 186 for powering system 101. Battery pack 186 facilitates field use of system 101 and provides a runtime of about 2 hours for continuous use, and about two days when left in a standby mode. For practical purposes, this runtime allows for system 101 to undertake the characterisation of about seventy-five samples.

In other embodiments alternative battery packs or batteries are used to provide different runtimes. Moreover, in some embodiments, system 101 includes a battery charger (not shown) that is disposed within cavity 103 for facilitating charging of the battery pack or other batteries.

Socket 214 is upwardly facing and inclined by about 20° with respect to the vertical for more clearly visibly presenting the socket to a user facing front wall 123. The small inclination of socket 214 offers only a small surface area of socket 214 for the accumulation of particulate matter and other contaminants that are often encountered during field use.

Socket 214 is, in use, electrically connected with battery pack 185 to allow external recharging of the battery and/or powering of system 101. As mentioned above, in some embodiments that charging is facilitated by an in-built charger, while in other embodiments an external charger is relied upon. In further embodiments battery pack 185 is removed for recharging.

It will be appreciated that other embodiments make use made of a power source other than a 12 Volt rechargeable lithium battery or a 12 Volt outlet of a car or other vehicle.

Duct 182 is attached to a ventilation drive device in the form of a low voltage DC circulation fan 184 that, in turn, is attached to cover 195 adjacent to inlet 202. Duct 183 is fixedly mounted to cover 195 adjacent to outlet 203. Ducts 182 and 183 are disposed adjacent to and on opposite sides of lamp 105 to define a ventilation path that commences at filter 207 and then sequentially progresses to inlet 202, fan 184, duct 182, lamp 105, duct 183, outlet 203 and filter 208. When fan 184 is actuated it draws air along the path to cool lamp 105. In this embodiment fan 184 is actuated to maintain lamp 105 within a predetermined range of operating temperatures to aid in the consistent output of radiation from lamp 105 which, in turn, contributes to the accuracy of the data provided by system 101. This also assists in prolonging the life of lamp 105 and therefore reducing the overall maintenance costs for system 101.

In this embodiment ducts 182 and 183 are quarter-cylindrical plastics channels. In other embodiments ducts 182 and 183 have alternative shapes and configurations.

In other embodiments, fan 184 runs continuously to maintain a constant flow of air along the path.

Body 102 also includes a rearwardly mounted elongate removable plastics service covering 215 for extending transversely across and sealingly snap-lockingly engaging with cover 195. Covering 215 overlies inlet 202, outlet 203 and aperture 204 and includes two transversely spaced apart vents 217 and 218 that are disposed substantially adjacent to, and which directly overlie, respective filters 207 and 208. Vents 217 and 218 include respective integrally formed plastic grids to act as first pass coarse particle filters. Covering 215, when snap-lockingly engaged with cover 195 clampingly maintains filters 207 and 208 within the inlet 202 and outlet 203 and abutted against respective flanges 205 and 206. Covering 215 also clamplingly retains receptacle 185 and battery 186 within aperture 204.

It will be appreciated by those skilled in the art, with the benefit of the teaching herein, that system 101 is substantially self-contained. However, the items most likely to require servicing include filters 207 and 208, and battery pack 186. All those items are easily accessible following the removal of covering 215 from cover 195.

It will be appreciated that in other embodiments covering 215 is engagable with cover 195 by other than snap-locking means. In further embodiments covering 215 is comprised of a plurality of separate coverings (not shown) that individually extend across aperture 204, inlet 202 and outlet 203.

Figure 23:
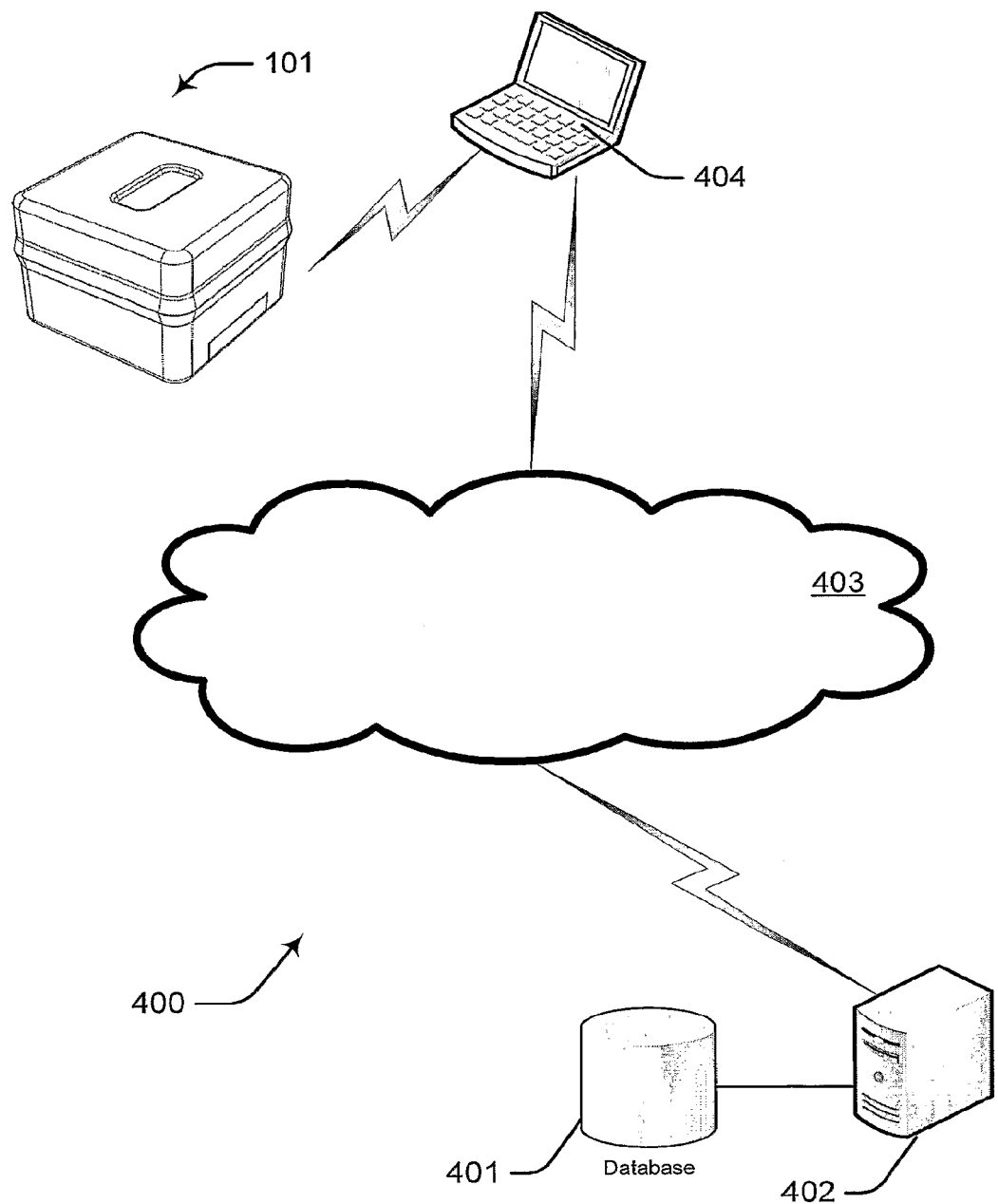

Receptacles 199,200 and 201 complimentarily receive respective tubular rectangular prismatic sample cartridges 219,220 and 221. A fourth tubular rectangular prismatic sample cartridge 222 is complementarily received within channel 104 by well 179 and underlies aperture 198. As best shown in FIG. 23, cartridges 219, 220, 221 and 222 each include two pairs of opposed sidewalls 223 and 224 that are integrally connected to form an open ended sample cavity 225 within channel 104. One pair of sidewalls 223 includes a pair of opposed generally circular glass windows 226 that are spaced apart by a predetermined distance for allowing substantially un-attenuated entry to and exit from cavity 225 of light from lamp 105. The predetermined distance between windows 226—which defines the minimum path length through the sample—is unique to each cartridge 219, 220, 221 and 222. Particularly, each cartridge is designed for samples of a specific and unique grain type, and to provide the light from source 105 with a specific distance to travel through the sample that is best suited for accurate measurement of the desired characteristic or characteristics for that grain type. The external dimensions of each of cartridges 219, 220, 221 and 222 are substantially identical for allowing interchanging of the cartridges within anyone of receptacles 199, 200 and 201 or well 179.

Cartridge 222 is designed for use with samples of wheat grains, and the path length between windows 226 is 18 mm. Cartridge 221, however, is designed for use with samples of canola grains, and the path length between windows 226 is 8 mm. It will be appreciated that in alternate embodiments there are more or less cartridges to cater for different grain types and which have different path lengths between windows 226.

In other embodiments windows 226 are rectangular, and are formed from other transparent material such as Perspex™. However, in other embodiments the windows are formed from BOROFLOAT™ Borosilicate, sapphire, BK7, or other optical grade glass.

While the above embodiments have been described with reference to the testing of grains, system 101 is also suitable for providing data indicative of one or more optically determined characteristics of other particulate materials such as processed foodstuffs, or small manufactured items such as polymer spheres and the like. Many other applications are also available. For example, in one such embodiment a system 101 is used to provide data indicative of the moisture content of a sample of a partially processed foodstuff. And only when the moisture content is within a predetermined range is that foodstuff further processed.

Figure 12:
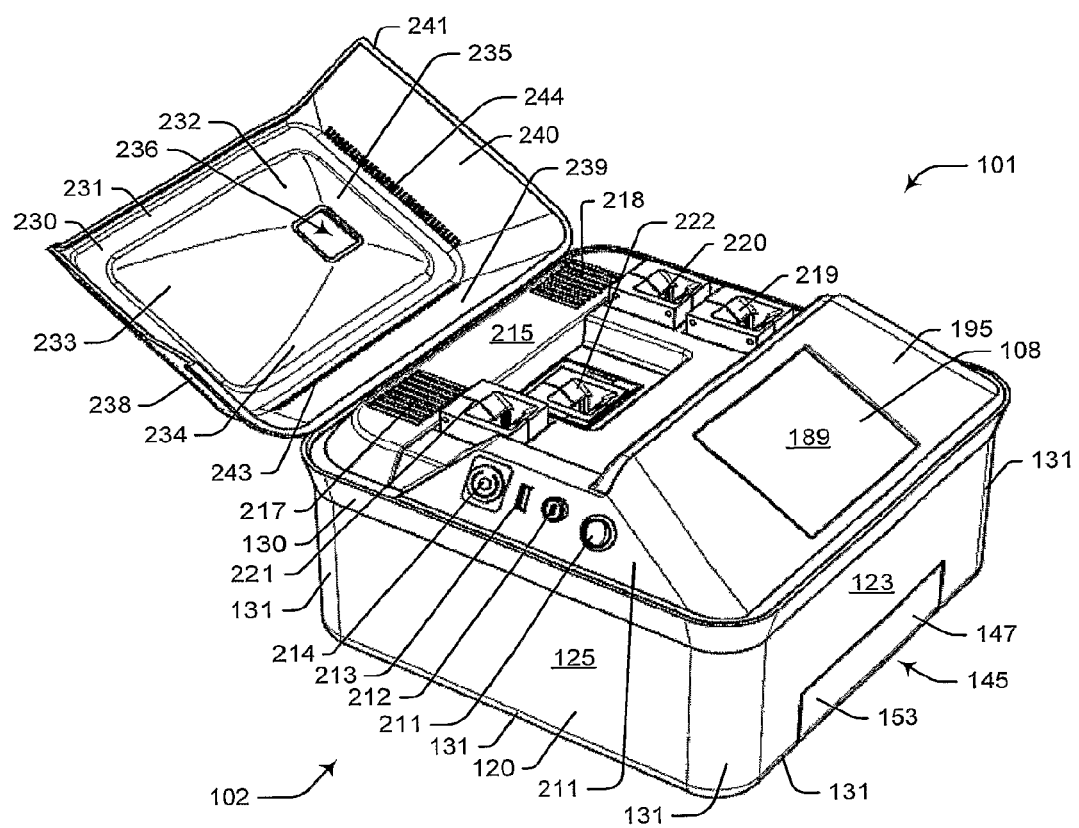
FIG. 12 is the system of FIG. 11 with the hopper shroud in an open configuration.
Figure 13:
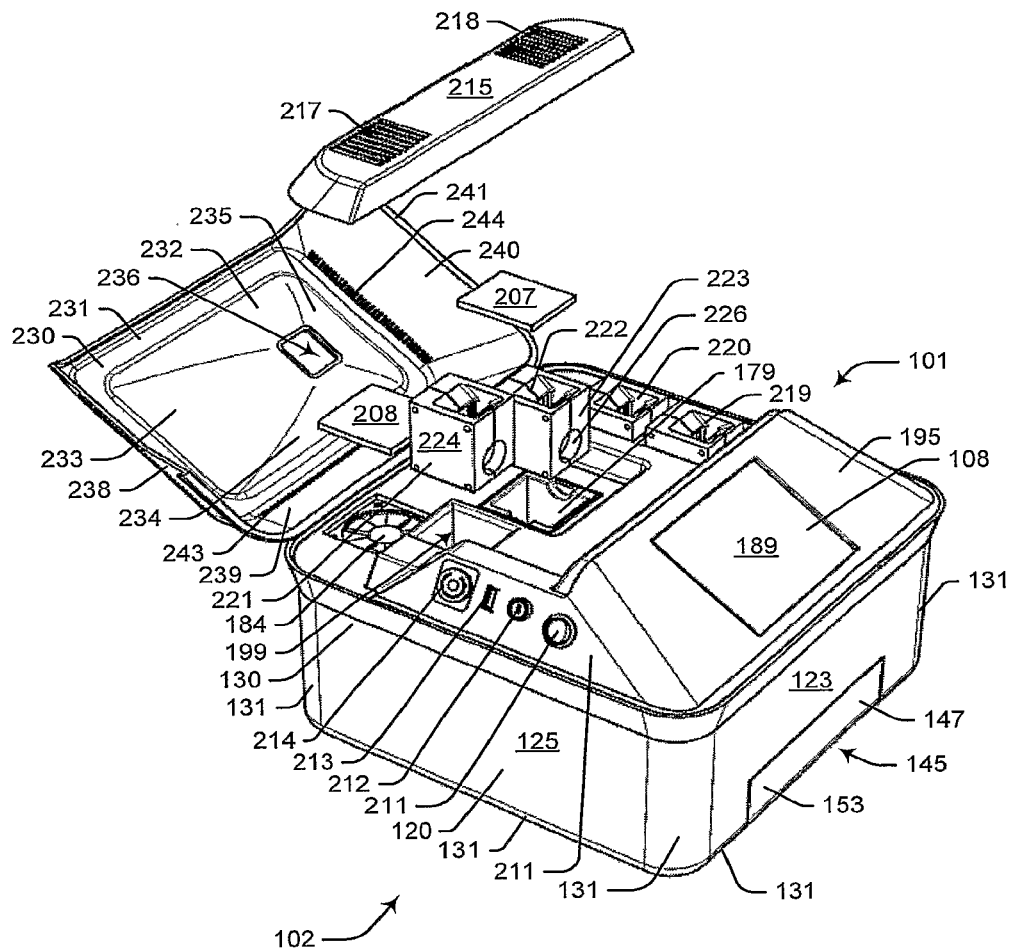
FIG. 13 is a partially exploded view of the system of FIG. 12.
Figure 14:
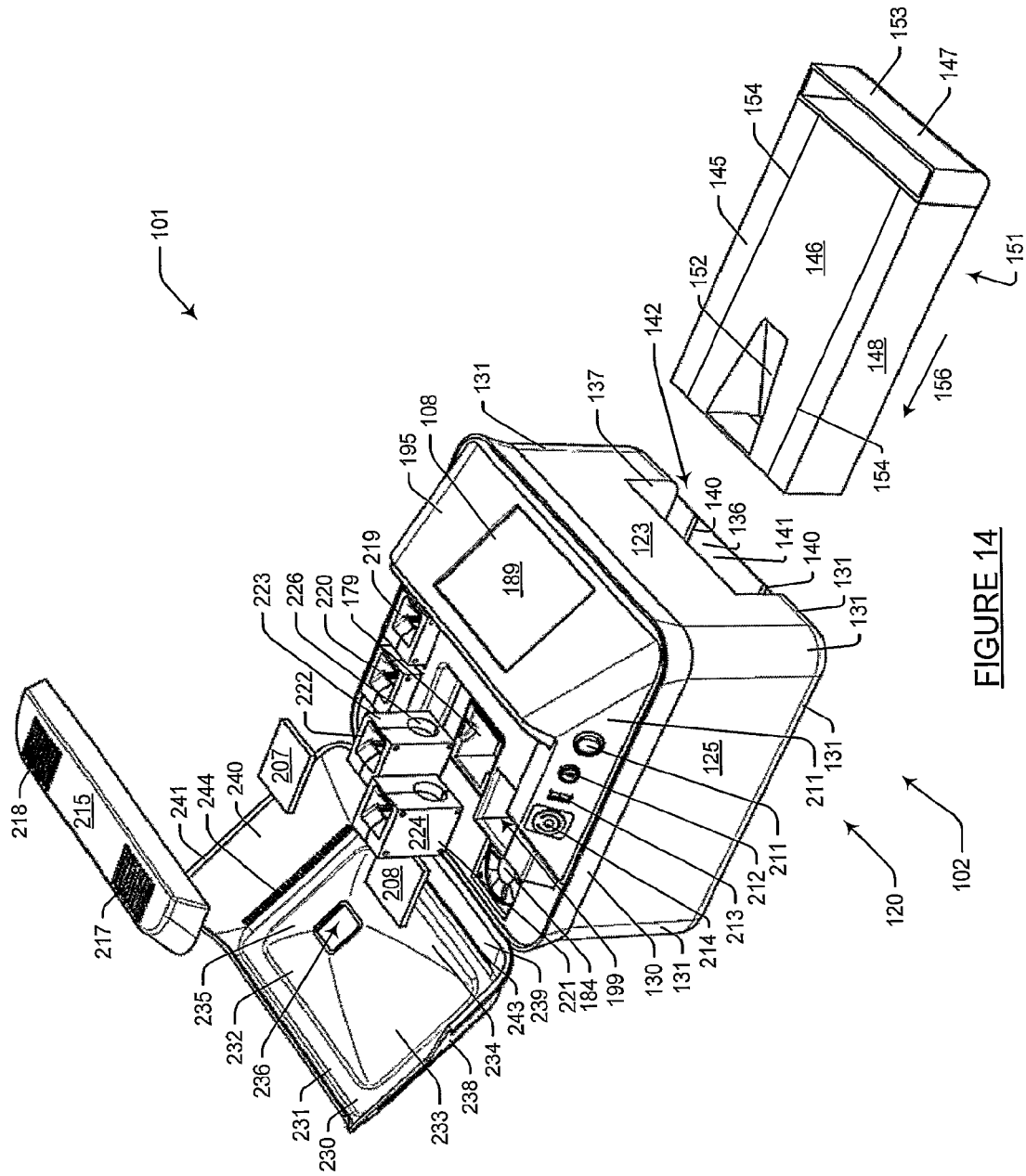
FIG. 14 is the system of FIG. 13 with the drawer removed from the body.
Figure 15:
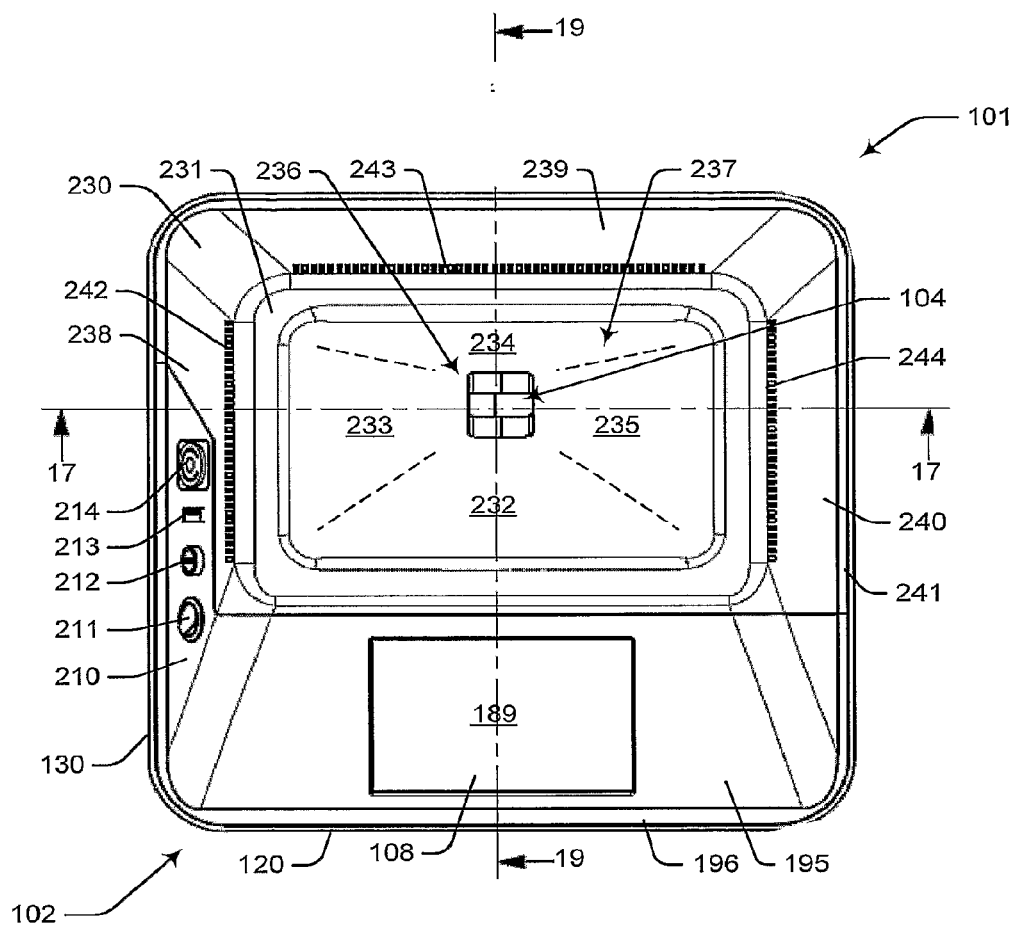
FIG. 15 is a top view of the system of FIG. 11.
Figure 16:
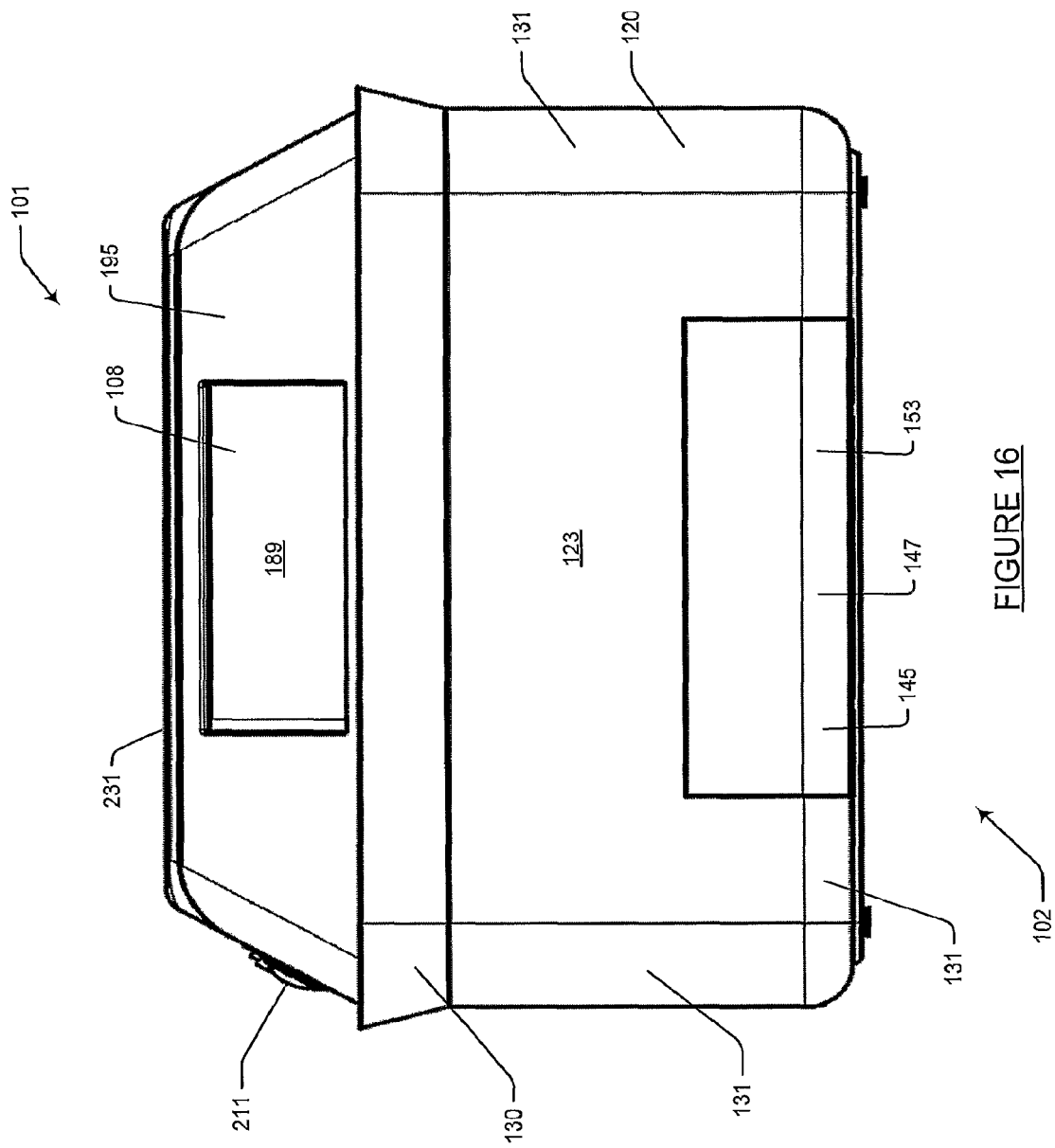
FIG. 16 is a front view of the system of FIG. 11.

As best shown in FIGS. 11 and 12, body 102 includes a moulded plastics hopper shroud 230 that houses the sample prior to entering channel 104. Shroud 230 includes a generally rectangular top rim 231 and four inclined hopper surfaces 232, 233, 234 and 235 which extend downwardly and inwardly from rim 231 and which terminate at an opening 236. The rim and the inclined surfaces define a hopper 237 that, as described below, is able to contain at least a predetermined volume of the sample. However, to do so, the sample is heaped within the hopper—in that the sample extends above rim 231—to limit the size of the sample. That is, hopper 231, when full to capacity, will include a volume of grain that is only just greater than the anticipated volume required to allow the twelve discrete measurements to be made.

In use, opening 236 overlies the upper end of channel 104 and, more particularly, overlies aperture 198. When the sample is disposed within hopper 237 it flows downwardly under the influence of gravity into aperture 198 and into channel 104. This flow is subject to control by the sample flow controller which, it will be recalled in this embodiment takes the form of gate assembly 175.

Shroud 230 further includes three integrally formed inclined outer sidewalls 238, 239 and 240 that are adjacent to respective surfaces 233, 234 and 235. Sidewalls 238, 239 and 240 extended downwardly and outwardly from rim 231 and terminate in a continuous sealing periphery 241. Periphery 241 is sealingly, releasably and snaplockingly engagable with cover 195 such that shroud 230 generally covers receptacles 199, 200 and 201 and apertures 202, 203 and 204. The sidewalls include respective elongate ventilation grating 242, 243 and 244 which extend substantially parallel with the adjacent rim 231.

It will be appreciated that other embodiments shroud 230 is differently shaped and/or configured. For example, in one embodiment (not shown) shroud 230 is an inclined chute or tunnel that extends between a first open end which is disposed on one side of body 102 to a second open end that immediately overlies aperture 198.

Hopper 237 has a volume of about 300 ml, but will contain about 400 ml of grain sample if that sample is heaped within the hopper. In other embodiments the volume of hopper 231 will be more or less than 300 mL The volume of receptacle 151 is preferably greater than the volume of grain that is able to be contained within hopper 231. In other embodiments volume of receptacle 151 is less than the volume of hopper 231.

System 101 includes a substantially rectangular prismatic downwardly opening plastics lid 250 for sealingly engaging with body 102. Lid 250 includes a generally horizontal roof 251 and four integral sidewalls 252 which extend downwardly from roof 251 and which terminating at an outwardly flared continuous lip 253. As shown in FIG. 9, lip 253 selectively lockingly sealingly engages with flange 130 to define a substantially water resistant closed configuration.

The intersection of adjacent sidewalls 252 together with the intersection of the sidewalls 252 with roof 251 takes the form of rounded corners 254. These corners, in conformity to those on unit 120, have a significant curvature—a radius of 20 about 10% of one side or 34 mm in this embodiment—to contribute to a robust housing both in terms of strength, and being less prone to inadvertently catching or snagging adjacent objects. The engagement of lip 253 with flange 130, and the like curvature of corners 254 with corners 131 is such that lid 250 lies flush with body 102 in the closed configuration.

Roof 251 and sidewalls 252 collectively define a storage cavity 255. Lid 250 includes a storage device in the form of a storage net (not shown) or storage bag (not shown) within cavity 255 for containing two coiled power cables (one such cable shown in FIG. 10 and denoted 257) for system 101. In further embodiments the storage device is an integrally formed compartment within cavity 255 and in yet further embodiments the storage device is an integrally formed reel disposed within cavity 255. In still further embodiments, the storage device is omitted and cable 257 is simply coiled loosely within cavity 255. It will be appreciated that one of the cables 257 includes a plug at one end for complementarily engaging with socket 214 and a plug at the other end for engaging with the 12 Volt power outlet of a vehicle, for example, a cigarette lighter socket of a vehicle. The other of the cables 257 is a mains power cable used with a transformer 258 for allowing system 101 to draw power from a mains power source, be that for powering system 101 directly or for allowing recharging of battery 186.

Roof 251 includes an integrally formed handle 259 to facilitate manual handling of system 101. In other embodiments handle 259 is not integrally formed and in further embodiments system 101 includes handles on one or more of the exposed surfaces of body 102.

Lid 250 and body 102 are generally square when viewed in plan and, as such, are inter-engagable in the closed configuration in one of four different relative rotational orientations. This also facilitates field use of system 101, as less regard has to be had to the precise relative orientation of lid 250 and body 102. In other embodiments lid 250 engages with body 102 by other means. For example, in one other embodiments lid 150 is hingedly attached to body 102.

System 101 includes two PCBs 261 and 262 that are mounted to chassis 157 within cavity 103 for supporting various electronic components associated with detection system 107, fan 184, gate assembly 175 and display 108. Tin shields 263 and 264 are mounted to chassis 157 and electromagnetically shield PCBs 261 and 262 respectively.

Figure 20:
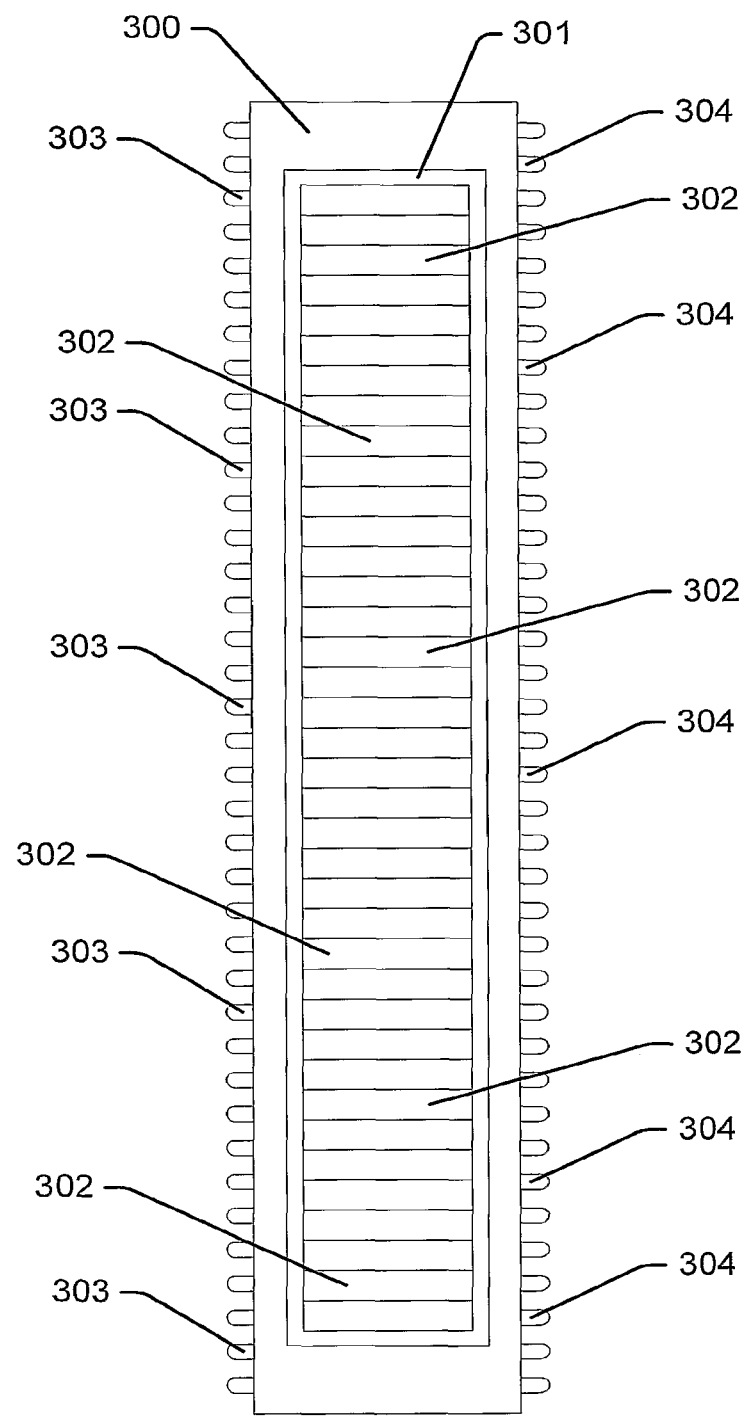
FIG. 20 is a schematic top view of an IC diode array.

Referring now to FIG. 21, an IC sensor 300 is disposed adjacent to plate 160 to detect light at the downstream end of path 162. As best shown in FIG. 20, sensor 300 includes a silicon base 301 and a linear array of thirty-eight individual pixels in the form of light-sensitive diodes 302 formed in base 301. It will be appreciated that diodes 302 are packaged underneath a transparent glass window. The packaging also includes two sets of oppositely disposed metallic legs 303 and 304 that are electrically engagable with PCB 162 for allowing each sensor 302 to be individual electrically connected on one side to a reference point (typically earth) and on the other side to an individual amplifier (not shown) that is disposed immediately adjacent to the respective diode.

Each of diodes 302 is responsive to light impinging upon it for providing a diode signal. In this embodiment the diode signal is a current that is generated by the respective diode in response to the intensity of light impinging upon the diode. The respective diode signals are provided to the individual amplifiers—that is, PCB 162 includes thirty-eight amplifiers—for providing respective amplified signals. A gain controller, in the form of the processor, selectively adjusts the gain of each amplifier to ensure all the amplified signals fall within a predetermined range, as will be described in more detail below. A 20-bit A/D converter (not shown) is mounted to PCB 161 immediately adjacent to the amplifiers and samples the amplified signals for providing one or more a sample signals. The processor is responsive to the gain of each amplifier and the sample signals for providing gain-adjusted data that is indicative of a characteristic parameter of the grain sample.

In other embodiments use is made of alternative A/D converters with different accuracies.

In use, one of the cartridges, and in this case cartridge 222, is received within and maintained adjacent to the upper end of channel 104 such that the windows 226 define a fore-aft path through channel 104 between lamp 105 and detection system 107. In the absence of the sample within the detection zone in channel 104, lamp 105 is activated to direct radiation along the fore-aft path and through the detection zone. This radiation then follows path 162 through detection system 107 and, subject to the optical processing by the intermediate optical components along path 162, impinges upon the thirty-eight diodes 302. The diodes, in turn, provide respective diode signals that are amplified by the respective amplifiers at a common gain $G_0$, to obtain a background reading sans sample. This background reading and $G_0$ are stored in memory associated with system 107.

Next, the sample flow controller, in the form of a metal gate assembly 195, is operated by the processor to progress from the retracted position where blade 178 is disposed within channel 104 as shown in FIG. 17, to the extended position where the distal end of blade 178 is received within notch 180. In the latter position, blade 178 is positioned to block the flow of the sample through channel 104.

The sample—in this instance about 400 ml of wheat grains—is then introduced into hopper 237 and progressively directed, under the influence of gravity, into channel 104. As blade 178 blocks the continued flow of the sample within the channel, only a given volume of the sample will progress into the channel. It will be appreciated that the fore-aft path defined between windows 226 of cartridge 222 is now partially obscured by the grains in the sample that are disposed between windows 226. The light that now follows path 161, and which subsequently impinges upon sensor 300, will have characteristics different to the light sans the presence of the sample within channel 104. Accordingly, the available diode signals will be attenuated from those taken sans the sample within channel 104, as would be understood by those skilled in the art. These most recent diode signals are amplified by the respective amplifiers at a gain of $G_0$ to provide amplified signals. The amplified signals are sampled to determine which of the 38 pixels provides the peak reading, and processor then calculates what gain would be required to have the peak reading at about 75% of the available range of the A/D converter. For a 20-bit A/D converter the range is about 0 to 1,048,576 and, as such, a level of about 750,000 is selected. Accordingly, if the peak detected was at 168,000, the gain of amplifiers for this measurement is set to approximately $G_0 \times (750,000/168,000)$. In some embodiments a separate gain calculation is determined for each pixel rather than for the pixel with the peak reading. In the embodiment, however, once the gain for the peak pixel is determined, that same gain is applied to all amplifiers. Moreover, the same gain will be retained for use with all twelve measurements for the sample. In other embodiments there is a recalculation of the gain for each separate measurement.

Following the sampling of the amplified signals by the A/D converter, there is a need to apply a correction factor to account for the gain that was applied by the amplifiers.

The diodes 302 in sensor 300 generate current levels in the order of μA, and the amplifiers provide a gain in the order of 1,000. The gain is provided by way of integration, in that the gain is increased or decreased by respectively increasing or decreasing the integration time of the amplifiers.

The amplifiers and the A/D converter are contained within a single IC (not shown) to minimise noise and signal loss.

In other embodiments, a suitable range is set for the amplified signals, where the range is bound by a low threshold $T_L$ and a high threshold $T_H$. The gain of the amplifier is then controlled by the processor to ensure that at least the peak, but in some embodiments all, amplified signals are within the range. In one embodiment, if the amplified signal is above or below the relevant threshold the gain for the particular amplifier is halved or doubled respectively. This has been found to provide a relatively time-effective and processor-effective approach to obtaining the desired gains for the amplifiers. In other embodiments—for example, where greater processing power is available—more complex algorithms are used to arrive at the gain for each amplifier. Where use is made of the gain doubling/halving regime that is described above it will be appreciated that $(2 \times T_L) < T_H$ to prevent an infinite loop being created.

To further enhance the practical aspects of system 101, and to make it even more suitable for field use, for each sample a plurality of data sets are obtained and averaged prior to an ultimate indication of the characteristic of the sample being supplied on display 189. In this embodiment, system 101 averages across ten data sets, while in other embodiments more or less data sets are used. In addition, system 101 gathers twelve data sets, and discards the highest and lowest values to arrive at the ten diode signals to be averaged.

In some embodiments use is made of a single amplifier in combination with a multiplexer that sequentially applies the diode signals to the input of the amplifier.

The auto-ranging function referred to above is embodied in system 101, where that system detects one or more predetermined characteristics of a grain sample and includes:

A detection zone 225 within channel 104 for containing the sample;

A radiation source in the form of lamp 105 for directing light into zone 225;

A plurality of detectors, in the form of the amplifiers, each of which provide a sensor signal, in the form of the amplified signals, in response to selected light emerging from zone 225;

A controller, in the form of the processor, that is responsive to the amplified signals for: selectively adjusting the detectors to provide respective adjusted amplified signals; and generating an adjustment signal in the form of a correction factor; and The processor, that is responsive to the adjusted amplified signals and the correction factor, for providing data indicative of the one or more predetermined characteristic of the sample.

It will also be appreciated that detection system 107 includes a processor, as described above, together with memory, one or more communication buses, power supply and regulation circuitry, and other components to allow operation of system 107. All these components are mounted to or connected with PCBs 261 and 263. It will be appreciated that system 107 employs operating software that is embedded or otherwise stored in the memory and selective executed. The processor is also configured to communicate selectively with an external computer or an external computer network (not shown) via port 213. In the present embodiment this communication occurs to:

Download from the network revised operating software that is subsequently embedded or stored within the memory instead of or in addition to the existing software.

Upload to the network from the memory operating details for system 101 or system 107. This includes any fault conditions or diagnostic data, together with details of any of the data indicative of the characteristics of the samples to allow further analysis of the data. In some embodiments, for example where the charge to the user of system 101 is based upon the number of samples characterised, the upload also includes data indicative of the number of samples.

Allow downloading of a virtual operating key that is required to unlock system 101 for operation. In some embodiments this key is date limited, in that the user pays for the key to be operable for a given period of time. Upon expiry of that period system 101 is disabled.

In other embodiments alternative ports or communication channels are included. For example, in some embodiments system 101 includes a wireless communication port for allowing wireless communication with remote devices.

It will be appreciated that base plate 160 is rigid and includes a sequence of formations, in the form of four recesses 11 to 14, for receiving respective optical components. The components define an optical path 162 that extends from an upstream end adjacent to formation 11 to a downstream end adjacent to recess 14. In other embodiments a different number of formations and/or components are used, although in the preferred embodiments the number of components are greater than or equal to two. Importantly, at least the first formation—that is, the upstream formation—sealingly receives its respective component. Preferably, both the upstream and the downstream components are sealingly received within respective formations. More preferably, all the components are respectively received within the formations.

Some of the advantages of the preferred embodiments include:

Allows cost-effective manufacture of an accurate and portable grain characterisation system as off-the-shelf components are able to be extensively used.

Robust housing and components together with lightweight and small size allow and facilitate field use.

Configured for standalone use and ease of access to a network for periodic servicing and/or calibration and/or software upgrades.

Cost efficient calibration, in that each individual system 101 does not need to be calibrated individually. That is, it is possible to build the instruments sufficiently similar to allow a single calibration to be developed for all the instruments. The instruments themselves become a variable in the calibration model.

Use of all injection moulded base plate of thermally stable material, which allows:
a. Relatively low cost manufacture.
b. Use of standard engineering tolerances.
c. Sufficient accuracy in maintaining the correct spatial relationships between optical components.
d. For a single initial adjustment of the optical components to provide the required optical path.

The use of pixels in the sensor that are relatively long in a direction normal to the direction of the initial adjustment. That is, the pixels of the preferred embodiments have a unit length of 1 in the direction of the adjustment, but a unit length of five in normal to the direction of the adjustment. By way of comparison, the beam diameter for the range of wavelengths of interest for each pixel typically is about 0.5 units.

Auto-ranging: which avoids the absorbance accuracy problem inherent in measurements of this type. It allows the A/D converter (or other detector) to continually operate in the optimal part of its response range. That is, it allows for two different samples having different absorbance to be subject to the same detector resolution.

Aligning of detector (which in the embodiment is sensor 300). That is, all that is required is a one-ff frequency adjustment to ensure that the pixels are correctly located relative to the light emerging from plate 160.

A light-weight system that is easily portable. Some embodiments weigh about 9 kg, while others are less than 8 kg. Moreover, the overall dimensions of system 101 are about 350 mm×350 mm×300 mm which makes it easy to store and secure, be that in a vehicle or elsewhere.

The functionality of various components—such as the processor, the IC sensor and others—have been described as being performed by distinct devices, such as dedicated integrated circuits. However, in preferred embodiments, all or any combination of their functionality is instead performed by multi-purpose integrated circuits or implemented in software executed on a microprocessor. Particularly in such cases, the invention is additionally embodied in a computer program or in a computer program in a data signal or stored on a data carrier.

Reference is now made to FIG. 23 where there is illustrated schematically a system 400, and where corresponding features are denoted by corresponding reference numerals. System 400 operates a set of optical characterisation instruments in the form of a plurality of distributed optical grain characterisation systems 101. While only one system 101 is illustrated it will be appreciated that system 400 includes many of systems 101, and in some embodiments supports many thousands of systems 101. Each system 101 includes operating software in the form of the software used to control the processor, and each provide operating data, in the form of the data characterising the grain sample and other data such as diagnostic data. System 400 includes a database 401 for maintaining data records indicative of systems 101, and a processor in the form of a central server 402 that is responsive to the data records for communicating with systems 101 to access and/or modify one or both of the operating data and the operating software.

In this embodiment the communication between server 402 and system 101 is via Internet 403 and a laptop computer 404. For other systems 101 the communication is via additional or alternative communication channels.

System 101 functions as described above to obtain data that is indicative of one or more characteristics of a grain sample. Such characteristics include moisture content, protein content, and others. The data is typically temporarily stored in memory within system 101, and periodically uploaded to an associated computer, such as laptop computer 404. In this embodiment computer 404 includes a locally loaded program that, when executed, provides a dedicated GUI for interacting with system 101. This GUI also facilitates interaction with server 402, and allows server 402 selected access to the data and to the operating software held in memory within systems 101.

A supplier of system 101 operates database 401 and server 402 to provide ongoing support and assistance to the party who has purchased, leased, entered into a hire purchase arrangement, or otherwise acquired the use of system 101 (referred to as "the acquiring party"). To that end, the records in database 401 include, amongst other things, data indicative of the serial number of system 1, the version of the operating system installed in system 101, and details of the acquiring party and the nature of the contract that has been entered into with the supplier. This allows the supplier to continue to develop the operating software and to have that offered to the acquiring party for automatic installation within system 101. This is particularly advantageous for those instances where the acquiring party leases the equipment for a given period, as any improvements are able to be quickly and easily propagated. For those instances where the acquiring party buys system 101, it is still possible to gain access to subsequent operating software, although typically subject to the payment of an agreed fee to the supplier. Operating software updates are more typically related to refinements to the operation of the auto-ranging and gain control, and the calibration of the optical system 107. However, in some instances more substantive operating software changes are required.

The ability for server 402 to communicate with system 101 has a number of security benefits including protection against theft during transit from the supplier to the acquiring party. For each system 101 requires a software key to operate, and that key only sent to system 101 once that particular system 101 is commissioned and dispatched, and an initial remote communication session established with server 402. In some embodiments such security measures are supplemented with additional measures such as sending a PIN separately to the acquiring party. In some embodiments, such as where the acquiring party is leasing system 101 from the supplier, the software key is only effective for allowing operation of system 101 up until a predetermined date. That is, the software key has an expiry date after which it is no longer effective. It will be appreciated that the expiry date in this instance is the final day of the period for which system 101 has been leased.

In other embodiments server 402 monitors the records in the database to determine when to communicate with systems 101 for maintenance and diagnostic purposes. That is, the operating data included within system 101 includes diagnostic data indicative of the performance of system 101. Server 402 selectively accesses this information to determine, for example, how many hours of operation the light source has had. If this is found to be approaching the limit of the accepted lifetime for the source, server 402 is responsive to the records in the database 401 for interfacing with an inventory and ordering system (not shown) to arrange for a replacement light source to be sent to the acquiring party.

In some embodiments the data indicative of the characteristics of the grain sample are automatically or selectively uploaded to server 402 to allow further analysis of that data. For example, in some instances the further analysis is to ascertain additional properties about the sample or samples on a pay-per-analysis basis, while in other instances the data is further analysed to provide verification of the ongoing accuracy of system 101. That is, the acquiring party is able to quickly, easily and accurately obtain data indicative of one or more predetermined characteristics of the sample. However, for some characteristics it is either not possible or not practical to undertake the required processing within system 101, and the necessary data is uploaded to server 402 to allow the additional analysis to occur. For example, one instance of additional analysis is to determine any correlation over a number of years between the protein content of a sample from a given area and the amount and cost of fertiliser applied to that area in those years. Another example is to look at correlations between protein content and the rainfall patterns.

In those embodiments where the operating data is appropriately coded and regularly uploaded to server 402, together with the other data, it is possible for such analysis to occur. Accordingly, system 101 is able to be used Fully off-line, in that it need not communicate with system 400.

In combination with system 400, but only in minimal communication with server 402 to, for example, receive updated operating software.

In combination with system 400, and in regular communication with server 402, to receive updated operating software, and to upload operating data for allowing, when required, additional more complicated analysis to occur.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

Although the invention has been described with reference to specific examples, it will be appreciated by those skilled in the art that it may be embodied in many other forms. In particular, features of anyone of the various described examples or embodiments may be provided in any combination in any of the other described examples or embodiments.

The invention claimed is:

1. A rigid base plate including a sequence of formations F1, F2, ..., Fn for receiving respective optical components C1, C2, ..., Cn to define an optical path, wherein n≥2 and at least the first formation F1 sealingly receives its respective component C1, wherein at least one of the optical components is a reflection diffraction grating, wherein at least one of the optical component is an optical barrel.

2. A base plate according to claim 1 wherein the last formation, Fn, sealingly receives component Cn.

3. A base plate according to claim 1, the base plate being at least partially defined by a mounting plate which at least partially defines the formations and a top plate for sealingly engaging with the mounting plate, wherein the mounting plate and the top plate collectively define a cavity for containing components C1, C2, ..., Cn.

4. A base plate according to claim 3 wherein the top plate and mounting plate each at least partially define the formations.

5. A base plate according to claim 4 wherein the mounting plate and the top plate substantially mirror each other.

6. A base plate according to claim 3 wherein the mounting plate and the top plate substantially mirror each other.

7. A base plate according to claim 3 wherein the mounting plate and the top plate include respective sealing faces that, in use, are abutted to effect the sealing engagement.

8. A base plate according to claim 3 wherein the mounting plate and the top plate collectively define along the path an entry window and an exit window.

9. A base plate according to claim 8 wherein F1 and Fn are adjacent to the entry window and the exit window respectively.

10. A rigid base plate according to claim 1, wherein: at least the first formation F1 is sealingly received to its respective component C1 by a sealing bead.

11. A rigid base plate according to claim 1 wherein the plate has a thickness of 12 mm.

12. A rigid base plate according to claim 1 wherein the plate has a rigidity greater than 2,000 MPa.

13. The plate of claim 1, wherein the optical barrel includes a pair of spaced apart convex lenses and circular aperture disposed intermediate the lenses, the lenses being equally displaced from the aperture.

14. The plate of claim 1 wherein at least one of the optical components is a focusing lens.

* * * * *